(12) United States Patent
Podack et al.

(10) Patent No.: US 9,238,064 B2
(45) Date of Patent: *Jan. 19, 2016

(54) ALLOGENEIC CANCER CELL-BASED IMMUNOTHERAPY

(71) Applicants: The University of Miami, Miami, FL (US); Nozomi Yamazaki, Sapporo (JP)

(72) Inventors: Eckhard R. Podack, Coconut Grove, FL (US); Joseph D. Rosenblatt, Hollywood, FL (US); Koichi Yamazaki, Sapporo (JP)

(73) Assignee: University of Miami, Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/930,818

(22) Filed: Jun. 28, 2013

(65) Prior Publication Data

US 2013/0302376 A1 Nov. 14, 2013

Related U.S. Application Data

(63) Continuation of application No. 12/921,151, filed as application No. PCT/US2009/001330 on Mar. 3, 2009, now Pat. No. 8,475,785.

(60) Provisional application No. 61/033,425, filed on Mar. 3, 2008.

(51) Int. Cl.

| A61K 39/00 | (2006.01) |
|---|---|
| A61K 39/385 | (2006.01) |
| A61K 45/06 | (2006.01) |
| A61K 35/13 | (2015.01) |
| C12N 5/09 | (2010.01) |
| C12N 5/16 | (2006.01) |
| A61K 35/12 | (2015.01) |

(52) U.S. Cl.
CPC .......... *A61K 39/0011* (2013.01); *A61K 35/12* (2013.01); *A61K 2039/5152* (2013.01); *A61K 2039/5156* (2013.01)

(58) Field of Classification Search
None
See application file for complete search history.

(56) References Cited

U.S. PATENT DOCUMENTS

| 4,215,051 A | 7/1980 | Schroeder et al. |
|---|---|---|
| 4,690,915 A | 9/1987 | Rosenberg |
| 5,108,921 A | 4/1992 | Low et al. |
| 5,137,819 A | 8/1992 | Kilburn |
| 5,168,062 A | 12/1992 | Stinski |
| 5,188,964 A | 2/1993 | McGuire |
| 5,202,247 A | 4/1993 | Kilburn |
| 5,217,891 A | 6/1993 | Brake |
| 5,232,833 A | 8/1993 | Sanders |
| 5,284,656 A | 2/1994 | Platz |
| 5,348,945 A | 9/1994 | Berberian |
| 5,385,839 A | 1/1995 | Stinski |
| 5,399,346 A | 3/1995 | Anderson |
| 5,444,087 A | 8/1995 | Patel |
| 5,451,569 A | 9/1995 | Wong et al. |
| 5,496,934 A | 3/1996 | Shoseyov |
| 5,580,859 A | 12/1996 | Felgner |
| 5,719,044 A | 2/1998 | Shoseyov |
| 5,747,332 A | 5/1998 | Wallen |
| 5,750,119 A | 5/1998 | Srivastava |
| 5,830,464 A | 11/1998 | Srivastava |
| 5,837,251 A | 11/1998 | Srivastava |
| 5,948,646 A | 9/1999 | Srivastava |
| 5,961,979 A | 10/1999 | Srivastava |
| 5,985,270 A | 11/1999 | Srivastava |
| 5,997,873 A | 12/1999 | Srivastava |
| 6,007,821 A | 12/1999 | Srivastava |
| 6,017,540 A | 1/2000 | Srivastava |
| 6,017,544 A | 1/2000 | Srivastava |
| 6,030,618 A | 2/2000 | Srivastava |
| 6,048,530 A | 4/2000 | Srivastava |
| 6,051,424 A | 4/2000 | Kato et al. |
| 6,130,087 A | 10/2000 | Srivastava |
| 6,136,315 A | 10/2000 | Srivastava |
| 6,156,302 A | 12/2000 | Srivastava |
| 6,162,436 A | 12/2000 | Srivastava |
| 6,168,793 B1 | 1/2001 | Srivastava |
| 6,322,790 B1 | 11/2001 | Srivastava |
| 6,328,957 B1 | 12/2001 | Colston et al. |

(Continued)

FOREIGN PATENT DOCUMENTS

| CA | 2158655 | 9/1994 |
|---|---|---|
| CN | 101057975 | 10/2009 |

(Continued)

OTHER PUBLICATIONS

Yamazaki et al (The Journal of Immunology, 1999, vol. 163, pp. 5178-5182).*

(Continued)

*Primary Examiner* — Karen Canella
(74) *Attorney, Agent, or Firm* — Fish & Richardson P.C.

(57) ABSTRACT

Cell-based immunotherapy (e.g., immunization or vaccination) may be improved by frequent administration to a human subject of allogeneic cancer cells secreting a modified heat shock protein (e.g., gp96), depletion of B cells in the subject, or both. Antigen (e.g., epitope derived from neoantigen or tumor antigen of allogeneic or syngeneic cancer cells) may induce a specific immune response in the subject. For example, the epitope bound in an immunogenic complex with the secreted heat shock protein may be obtained from allogeneic cancer cells coexpressing both secreted gp96 and antigen, or from syngeneic cancer cells of the subject expressing only antigen.

18 Claims, No Drawings

(56) References Cited

U.S. PATENT DOCUMENTS

| | | |
|---|---|---|
| 6,331,299 B1 | 12/2001 | Rothman et al. |
| 6,335,170 B1 | 1/2002 | Orntoft |
| 6,383,493 B1 | 5/2002 | Srivastava |
| 6,383,494 B1 | 5/2002 | Srivastava |
| 6,387,374 B1 | 5/2002 | Srivastava |
| 6,399,070 B1 | 6/2002 | Srivastava |
| 6,403,095 B1 | 6/2002 | Srivastava |
| 6,406,700 B1 | 6/2002 | Srivastava |
| 6,410,026 B1 | 6/2002 | Srivastava |
| 6,410,027 B1 | 6/2002 | Srivastava |
| 6,410,028 B1 | 6/2002 | Srivastava |
| 6,436,404 B1 | 8/2002 | Srivastava |
| 6,447,780 B1 | 9/2002 | Srivastava |
| 6,447,781 B1 | 9/2002 | Srivastava |
| 6,451,316 B1 | 9/2002 | Srivastava |
| 6,455,048 B1 | 9/2002 | Srivastava |
| 6,455,503 B1 | 9/2002 | Srivastava |
| 6,461,615 B1 | 10/2002 | Srivastava |
| 6,468,540 B1 | 10/2002 | Srivastava |
| 6,475,490 B1 | 11/2002 | Srivastava |
| 6,605,464 B1 | 8/2003 | Rothman |
| 6,610,659 B1 | 8/2003 | Pramod |
| 6,641,812 B2 | 11/2003 | Rothman |
| 6,651,655 B1 | 11/2003 | Licalsi et al. |
| 6,656,679 B2 | 12/2003 | Rothman |
| 6,663,868 B1 | 12/2003 | Rothman |
| 6,673,348 B2 | 1/2004 | Rothman |
| 6,719,974 B1 | 4/2004 | Rothman |
| 6,761,892 B1 | 7/2004 | Rothman |
| 6,797,480 B1 | 9/2004 | Srivastava |
| 6,797,491 B2 | 9/2004 | Neefe et al. |
| 6,905,827 B2 | 6/2005 | Wohlgemuth et al. |
| 7,026,121 B1 | 4/2006 | Wohlgemuth et al. |
| 7,132,109 B1 | 11/2006 | Srivastava |
| 7,235,358 B2 | 6/2007 | Wohlgemuth et al. |
| 7,601,359 B1 | 10/2009 | Srivastava |
| 7,931,896 B2 | 4/2011 | Chen |
| 7,989,173 B2 | 8/2011 | Chen |
| 8,101,349 B2 | 1/2012 | Garcia et al. |
| 8,475,785 B2 | 7/2013 | Podack et al. |
| 8,685,384 B2 | 4/2014 | Podack et al. |
| 8,747,833 B2 | 6/2014 | Chen et al. |
| 8,865,653 B2 | 10/2014 | Zitvogel et al. |
| 8,877,204 B2 | 11/2014 | Srivastava et al. |
| 2003/0133930 A1 | 7/2003 | Goldenberg |
| 2003/0170756 A1* | 9/2003 | Berd ............ 435/7.23 |
| 2003/0203846 A1 | 10/2003 | Srivastava et al. |
| 2004/0039156 A1 | 2/2004 | Segal et al. |
| 2004/0052812 A1 | 3/2004 | Hoe et al. |
| 2004/0091503 A1 | 5/2004 | Segal et al. |
| 2004/0136950 A1 | 7/2004 | Ni et al. |
| 2004/0136951 A1 | 7/2004 | Ni et al. |
| 2004/0253228 A1 | 12/2004 | Srivastava |
| 2005/0003484 A1 | 1/2005 | Hirano et al. |
| 2005/0019752 A1 | 1/2005 | Franchini |
| 2005/0129616 A1 | 6/2005 | Salcedo et al. |
| 2005/0129699 A1 | 6/2005 | Salcedo et al. |
| 2005/0214205 A1 | 9/2005 | Salcedo et al. |
| 2005/0214206 A1 | 9/2005 | Salcedo et al. |
| 2005/0214207 A1 | 9/2005 | Salcedo et al. |
| 2005/0214208 A1 | 9/2005 | Salcedo et al. |
| 2005/0214209 A1 | 9/2005 | Salcedo et al. |
| 2005/0214210 A1 | 9/2005 | Salcedo et al. |
| 2005/0221395 A1 | 10/2005 | Zabrecky et al. |
| 2005/0233958 A1 | 10/2005 | Ni et al. |
| 2005/0244857 A1 | 11/2005 | Ni et al. |
| 2006/0062786 A1 | 3/2006 | Salcedo et al. |
| 2006/0079458 A1 | 4/2006 | Srivastava et al. |
| 2006/0093612 A1 | 5/2006 | Srivastava |
| 2006/0148064 A1 | 7/2006 | Srivastava |
| 2006/0270837 A1 | 11/2006 | Salcedo et al. |
| 2007/0141666 A1 | 6/2007 | Dupraz |
| 2007/0292411 A1 | 12/2007 | Salcedo et al. |
| 2007/0298041 A1 | 12/2007 | Tomlinson |
| 2008/0019972 A1 | 1/2008 | Andrieu |
| 2008/0026012 A1 | 1/2008 | Podack et al. |
| 2008/0038316 A1 | 2/2008 | Wong et al. |
| 2008/0089901 A1 | 4/2008 | Hanke |
| 2008/0241155 A1 | 10/2008 | Ni et al. |
| 2008/0248046 A1 | 10/2008 | Ni et al. |
| 2009/0148471 A1 | 6/2009 | Wu et al. |
| 2009/0162404 A1 | 6/2009 | Podack |
| 2010/0080773 A1 | 4/2010 | Geho et al. |
| 2010/0297154 A1 | 11/2010 | Segal |
| 2011/0053829 A1 | 3/2011 | Baumhof et al. |
| 2011/0059041 A1 | 3/2011 | Truneh et al. |
| 2011/0111006 A1 | 5/2011 | Wong et al. |
| 2011/0171211 A1 | 7/2011 | Podack |
| 2011/0212090 A1 | 9/2011 | Pedersen et al. |
| 2011/0223196 A1 | 9/2011 | Podack et al. |
| 2011/0250229 A1 | 10/2011 | Podack |
| 2011/0287057 A1 | 11/2011 | Podack |
| 2012/0034242 A1 | 2/2012 | Jooss et al. |
| 2012/0100173 A1 | 4/2012 | Leclair et al. |
| 2012/0258046 A1 | 10/2012 | Mutzke |
| 2013/0045202 A1 | 2/2013 | Irving et al. |
| 2013/0052160 A1 | 2/2013 | Zitvogel et al. |
| 2014/0037682 A1 | 2/2014 | Podak et al. |
| 2014/0134650 A1 | 5/2014 | Hawtin et al. |
| 2014/0286991 A1 | 9/2014 | Podack et al. |
| 2014/0335050 A1 | 11/2014 | Haggerty et al. |
| 2014/0335086 A1 | 11/2014 | Podack |

FOREIGN PATENT DOCUMENTS

| | | |
|---|---|---|
| CN | 102223894 | 10/2011 |
| DE | 19602985 | 7/1997 |
| EP | 1280900 | 7/2009 |
| EP | 1603936 | 4/2012 |
| EP | 1573047 | 11/2013 |
| EP | 2331129 | 6/2014 |
| GB | 2251186 | 7/1992 |
| JP | 2002-506005 | 2/2002 |
| JP | 2007-532681 | 11/2007 |
| WO | WO8912455 | 12/1989 |
| WO | WO9002564 | 3/1990 |
| WO | WO9102077 | 2/1991 |
| WO | WO9115572 | 10/1991 |
| WO | WO9201717 | 2/1992 |
| WO | WO9208484 | 5/1992 |
| WO | WO9208488 | 5/1992 |
| WO | WO9314118 | 7/1993 |
| WO | WO9317712 | 9/1993 |
| WO | WO9318146 | 9/1993 |
| WO | WO9318147 | 9/1993 |
| WO | WO9321529 | 10/1993 |
| WO | WO9403208 | 2/1994 |
| WO | WO9403599 | 2/1994 |
| WO | WO9404676 | 3/1994 |
| WO | WO9411513 | 5/1994 |
| WO | WO9500654 | 1/1995 |
| WO | WO9504824 | 2/1995 |
| WO | WO9506725 | 3/1995 |
| WO | WO9522618 | 8/1995 |
| WO | WO9524923 | 9/1995 |
| WO | WO9601611 | 1/1996 |
| WO | WO9602143 | 2/1996 |
| WO | WO9610411 | 4/1996 |
| WO | WO9610419 | 4/1996 |
| WO | WO9631613 | 10/1996 |
| WO | WO9706685 | 2/1997 |
| WO | WO9706821 | 2/1997 |
| WO | WO9706828 | 2/1997 |
| WO | WO9710000 | 3/1997 |
| WO | WO9710001 | 3/1997 |
| WO | WO9710002 | 3/1997 |
| WO | WO9726910 | 7/1997 |
| WO | WO9735619 | 10/1997 |
| WO | WO9823735 | 6/1998 |
| WO | WO9942121 | 8/1999 |
| WO | WO0054437 | 9/2000 |
| WO | WO03005964 | 1/2003 |
| WO | WO 03042661 | 5/2003 |
| WO | WO 2004016753 | 2/2004 |

(56) References Cited

FOREIGN PATENT DOCUMENTS

| WO | WO2004032865 | | 4/2004 |
| WO | WO 2004078921 | | 9/2004 |
| WO | WO 2005016236 | | 2/2005 |
| WO | WO2005/030136 | * | 4/2005 |
| WO | WO2005092373 | | 10/2005 |
| WO | WO2005113003 | | 12/2005 |
| WO | WO2005120558 | | 12/2005 |
| WO | WO 2007030531 | | 3/2007 |
| WO | WO 2009018500 | | 2/2009 |
| WO | WO2009114085 | | 9/2009 |
| WO | WO2009117116 | | 9/2009 |
| WO | WO2009118247 | | 10/2009 |
| WO | WO2009118733 | | 10/2009 |
| WO | WO2009121483 | | 10/2009 |
| WO | WO 2010060026 | | 5/2010 |
| WO | WO2010081738 | | 7/2010 |
| WO | WO 2010088927 | | 8/2010 |
| WO | WO 2010115118 | | 10/2010 |
| WO | WO 2011069528 | | 6/2011 |
| WO | WO 2011109789 | | 9/2011 |
| WO | WO2011146828 | | 11/2011 |
| WO | WO 2012166617 | | 12/2012 |
| WO | WO 2014140884 | | 9/2014 |
| WO | WO 2014140904 | | 9/2014 |

OTHER PUBLICATIONS

Podack et al (Expert Opinion on Biological Therapy, 2007, vol. 7, pp. 1679-1688).*

Abstract of Oizumi et al (Proc. Amer. Assoc. Cancer Res., 2006, vol. 47, Abstract# 3136.*

"Novel Tumor Vaccine gp96-Ig Fusion Protein in Advanced (Stage IIIB), Relapsed or Metastatic (Stage IV) Non-Small Cell Lung Cancer (NSCLC) Patients Who Have Failed First Line Chemotherapy," ClinicalTrials.gov archive, [online] Dec. 27, 2007 [retrieved on Jan. 14, 2014]. Retrieved from the Internet: <URL: http://clinicaltrials.gov/archive/NCT00503568/2007_12_27>, 4 pages.

Arnold et al., "Influences of transporter associated with antigen processing (TAP) on the repertoire of peptides associated with the endoplasmic reticulum-resident stress protein gp96," J. Exp. Med., 186(3):461-466, Aug. 4, 1997.

Barrios et al., "Heat shock proteins as carrier molecules: in vivo helper effect mediated by Escherichia coli GroEL and DnaK proteins requires cross-linking with antigen," Clin Exp Immunol, 98(2):229-233, Nov. 1994.

Barrios et al., "Specificity of antibodies induced after immunization of mice with the mycobacterial heat shock protein of 65 kD," Clin Exp Immunol, 98(2):224-8, Nov. 1994.

Blachere et al., "Heat shock protein-peptide complexes, reconstituted in vitro, elicit peptide-specific cytotoxic T lymphocyte response and tumor immunity," J Exp Med., 186(8):1315-1322, Oct. 20, 1997.

Bodey et al, "Failure of cancer vaccines: the significant limitations of this approach to immunotherapy," Anticancer Res., 20(4):2665-2676, Jul.-Aug. 2000.

Boon, "Toward a genetic analysis of tumor rejection antigens," Advances in Cancer Research, 1992, vol. 58: 177-210.

Breloer et al. "Isolation of processed, H-2Kb-binding ovalbumin-derived peptides associated with the stress proteins HSP70 and gp96" Eur. J. Immunol., 28(3):1016-1021, Mar. 1998.

Burton and Moore, "Why do we not have an HIV vaccine and how can we make one?," Nature Medicine, 4:495-498, 1998.

Dai et al., "Cell surface expression of heat shock protein gp96 enhances cross-presentation of cellular antigens and the generation of tumor-specific T cell memory," Cancer Immun., 3:1, Jan. 28, 2003.

de Gruijl and Curiel, "Cancer vaccine strategies get bigger and better,"Nat Med., 5(10):1124-1125, Oct. 1999.

Desrosiers, "Prospects for an AIDS vaccine," Nat Med., 10(3):221-223, Mar. 2004.

Evans and Kaye, "Vaccine therapy for cancer-fact or fiction?" Q. J. Med. 92(6):299-307, Jun. 1999.

Ezzell, "Cancer 'vaccines': an idea whose time has come?", The Journal of Research, 7:46-49, Jan. 1995.

Gaiger et al., "Immunity to WT1 in the animal model and in patients with acute myeloid leukemia," Blood, 96(4):1480-1489, Aug. 15, 2000.

Girard et al., "A review of vaccine research and development: the human immunodeficiency virus (HIV)," Vaccine, 24(19):4062-4081, Epub Feb. 28, 2006.

Gullo and Teoh, "Heat shock proteins: to present or not, that is the question," Immunol Lett., 94(1-2):1-10, Jun. 15, 2004.

Heike et al., "Heat shock protein-peptide complexes for use in vaccines," J Leukoc Biol., 60(2):153-158, Aug. 1996.

Inoue et al., "Inhibitory effects of B cells on antitumor immunity," Cancer Res., 66(15):7741-7747, Aug. 1, 2006.

Jakob et al., "Small heat shock proteins are molecular chaperones," J Biol Chem., 268(3):1517-1520, Jan. 25, 1993.

Janetzki et al., "Immunization of cancer patients with autologous cancer-derived heat shock protein gp96 preparations: a pilot study," Int J Cancer, 88(2):232-238, Oct. 15, 2000.

Kovalchin et al., "Determinants of efficacy of immunotherapy with tumor-derived heat shock protein gp96," Cancer Immun., 1:7, 9 pages, Apr. 27, 2001.

Lakey et al., "Identification of a peptide binding protein that plays a role in antigen presentation," Proc Natl Acad Sci USA, 84(6):1659-1663, Mar. 1987.

Li and Srivastava, "Tumor rejection antigen gp96/grp94 is an ATPase: implications for protein folding and antigen presentation," EMBO J., 12(8):3143-3151, Aug. 1993.

Li et al., "Heat shock protein 70 fused to or complexed with hantavirus nucleocapsid protein significantly enhances specific humoral and cellular immune responses in C57BL/6 mice," Vaccine, 26(25):3175-3187, Epub Mar. 20, 2008.

Lindquist and Craig, "The heat-shock proteins," Annu. Rev. Genet., 22:631-677, 1988.

Lukacs et al, "In vivo gene therapy of malignant tumours with heat shock protein-65 gene" Gene Ther., 4(4):346-350, Apr. 1997.

Lukacs et al., "Tumor cells transfected with a bacterial heat-shock gene lose tumorigenicity and induce protection against tumors," J Exp Med., 178(1):343-348, Jul. 1, 1993.

Maki et al., "Human homologue of murine tumor rejection antigen gp96: 5'-regulatory and coding regions and relationship to stress-induced proteins," Proc Natl Acad Sci USA, 87(15):5658-5662, Aug. 1990.

Matthews et al., "Prospects for development of a vaccine against HTLV-III-related disorders," AIDS Res Hum Retroviruses, 3 Suppl 1:197-206, 1987.

Meerovitch et al., "Proparathyroid hormone-related protein is associated with the chaperone protein BiP and undergoes proteasome-mediated degradation," J Biol Chem., 273(33):21025-21030, Aug. 14, 1998.

Multhoff et al., "Heat shock protein 72 on tumor cells: a recognition structure for natural killer cells," J Immunol., 158(9):4341-4350, May 1, 1997.

Nicchitta, "Biochemical, cell biological and immunological issues surrounding the endoplasmic reticulum chaperone GRP94/gp96," Curr Opin Immunol., 10(1):103-109, Feb. 1998.

Oizumi and Podack, "Important role of heat shock protein gp96-chaperoned peptides in efficient cross priming of CD8 T cells by rapid recruitment and activation of DC and NK cells," Proc Amer Assoc Cancer Res., vol. 47, Abstract# 3136, 2006.

Oizumi et al., "Molecular and cellular requirements for enhanced antigen cross-presentation to CD8 cytotoxic T lymphocytes," J Immunol., 179(4):2310-2317, Aug. 15, 2007.

Oizumi et al., "Surmounting tumor-induced immune suppression by frequent vaccination or immunization in the absence of B cells," J Immunother., 31(4):394-401, May 2008.

Philip et al., "Efficient and sustained gene expression in primary T lymphocytes and primary and cultured tumor cells mediated by adeno-associated virus plasmid DNA complexed to cationic liposomes," Mol Cell Biol., 14(4):2411-2418, Apr. 1994.

Pidoux and Armstrong, "Analysis of the BiP gene and identification of an ER retention signal in Schizosaccharomyces pombe," EMBO J., 11(4):1583-1591, Apr. 1992.

(56) References Cited

OTHER PUBLICATIONS

Podack et al, "Mucosal HIV immunity generated by gp96-SIV/HIV peptide complexes secreted by allogeneic cell," *AIDS Research and Human Retroviruses*, vol. 24, No. Suppl. 1, p. 91, Abstract p. 11-18, Oct. 2008.
Podack et al., "Allogeneic tumor-cell-based vaccines secreting endoplasmic reticulum chaperone gp96," *Expert Opin. Biol. Ther.*, 7(11):1679-1688, Nov. 2007.
Podack et al., "Immunotherapy for lung tumors: M17-01," *J Thorac Oncol*, 2(8)Suppl 4: S197-S198, 3 pages, Aug. 2007.
Raez et al., "Lung cancer immunotherapy," *Clin Med Res.*, 3(4):221-228, Nov. 2005.
Segal et al., "Heat shock proteins as vaccine adjuvants in infections and cancer," *Drug Discov Today*, 11(11-12):534-540, Jun. 2006.
Spitler, "Cancer vaccines: the interferon analogy," Cancer Biother., 10(1):1-3, Spring 1995.
Srivastava and Old, "Identification of a human homologue of the murine tumor rejection antigen GP96," *Cancer Res.*, 49(6):1341-1343, Mar. 15, 1989.
Srivastava et al., "Chromosomal assignment of the gene encoding the mouse tumor rejection antigen gp96," *Immunogenetics*, 28(3):205-207, 1988.
Srivastava et al., "Heat shock proteins transfer peptides during antigen processing and CTL priming," *Immunogenetics*, 39(2):93-98, 1994.
Srivastava et al., "Tumor rejection antigens of chemically induced sarcomas of inbred mice," *Proc Natl Acad Sci U S A*, 83(10):3407-3411, May 1986.
Strbo and Podack, "Secreted heat shock protein gp96-Ig: an innovative vaccine approach," *Am J Reprod Immunol.*, 59(5):407-416, May 2008.
Strbo et al., "Cell-secreted Gp96-Ig-peptide complexes induce lamina propria and intraepithelial CD8+ cytotoxic T lymphocytes in the intestinal mucosa," *Mucosal Immunol.*, 3(2):182-192, Mar. 2010.
Strbo et al., "Gp96SIV Ig immunization induces potent polyepitope specific, multifunctional memory responses in rectal and vaginal mucosa," *Vaccine*, 29(14):2619-2625, Mar. 2011.
Strbo et al., "HLA A2 restricted HIV specific mucosal and systemic immunity induced with secreted heat shock protein gp96-Ig," FASEB J, 22:856.21, 2008.
Strbo et al., "OAO5-04. Gp96-Ig-SIV vaccines induce predominant immune responses at mucosal sites," *Retrovirology*, 6(Suppl 3):O34, Oct. 22, 2009.
Strbo et al., "Secreted gp96-ig mediates CD8 and NK cell expansion," Experimental Biology 2002: Meeting Abstracts, *FASEB J*, 16(4):A336, Abstract 246.21, 2002.
Strbo et al., "SIV-Gp96-Ig vaccine induces high levels of adaptive mucosal CD8 effector cells in Rhesus macaques", *J Med Primatol*, 39(4):272, Abstract 19, Aug. 2010, 27th Annual Symposium on Non-human Primate Models for AIDS, Boston, MA, Oct. 28-31, 2009.
Strbo et al.,"Heat shock fusion protein gp96-Ig mediates strong CD8 CTL expansion in vivo," *Am J Reprod Immunol.*, 48(4):220-225, Oct. 2002.
Udono and Srivastava, "Heat shock protein 70-associated peptides elicit specific cancer immunity," *J Exp Med.*, 178(4):1391-1396, Oct. 1, 1993.
Udono et al., "Cellular requirements for tumor-specific immunity elicited by heat shock proteins: tumor rejection antigen gp96 primes CD8+ T cells in vivo," *Proc Natl Acad Sci U S A.*, 91(8):3077-3081, Apr. 12, 1994.
Ullrich et al., "A mouse tumor-specific transplantation antigen is a heat shock-related protein," *Proc Natl Acad Sci U S A.*, 83(10):3121-3125, May 1986.
Van den Eynde et al., "The gene coding for a major tumor rejection antigen of tumor P815 is identical to the normal gene of syngeneic DBA/2 mice," *J Exp Med.*, 173(6):1373-1384, Jun. 1, 1991.
Vanbuskirk et al., "A peptide binding protein having a role in antigen presentation is a member of the HSP70 heat shock family," *J Exp Med.*, 170(6):1799-1809, Dec. 1, 1989.
Viitanen et al., "Mammalian mitochondrial chaperonin 60 functions as a single toroidal ring," *J Biol Chem.*, 267(2):695-698, Jan. 15, 1992.
Wang et al., "Characterization of heat shock protein 110 and glucose-regulated protein 170 as cancer vaccines and the effect of fever-range hyperthermia on vaccine activity," *J Immunol.*, 166(1):490-497, Jan. 1, 2001.
Welch and Feramisco, "Purification of the major mammalian heat shock proteins," *J Biol Chem.*, 257(24):14949-14959, Dec. 25, 1982.
Wheeler, "Preventive vaccines for cervical cancer," *Salud Publica Mex.*, 39(4):283-287, Jul.-Aug. 1997.
Yamazaki et al, "Induction of tumor immunity by gp96 secreted from engineered tumor cells," *Lung Cancer*, 29(1 Suppl. 1):185, Abstract 623, XP027413932, presented Sep. 13, 2000.
Yamazaki et al., "Cutting edge: tumor secreted heat shock-fusion protein elicits CD8 cells for rejection," *J Immunol.*, 163(10):5178-5182, Nov. 15, 1999.
Young, "Stress proteins and immunology," Annu Rev Immunol., 8.401-420, 1990.
Yu and Fang, "Clinical trials with oncolytic adenovirus in China," *Curr Cancer Drug Targets.*, 7(2):141-148, Mar. 2007.
Zheng et al., "Cell surface targeting of heat shock protein gp96 induces dendritic cell maturation and antitumor immunity," *J Immunol.*, 167(12):6731-6735, Dec. 15, 2001.
Zinn et al., "Regulated expression of an extrachromosomal human beta-interferon gene in mouse cells," *Proc Natl Acad Sci U S A.*, 79(16):4897-4901, Aug. 1982.
Zügel et al., "gp96-peptide vaccination of mice against intracellular bacteria," Infect Immun., 69(6):4164-4167, Jun. 2001.
"Vaccine therapy in treating patients with Stage III, Stage IV, or relapsed non-small cell lung cancer treated with first-line chemotherapy," Jul. 18, 2007. Retrieved from the Internet: URL: http://clinicaltrials.gov/archive/NCT00503568.
Abbas et al., "Functional diversity of helper T lymphocytes," *Nature*, 383(6603):787-793, Oct. 1996.
Adams et al., "Molecular cloning of mouse immunoglobulin heavy chain messenger ribonucleic acids coding for mu, alpha, gamma 1, gamma 2a, and gamma 3 chains," *Biochemistry*, 19(12):2711-2719, Jun. 10, 1980.
Adams et al., "The c-myc oncogene driven by immunoglobulin enhancers induces lymphoid malignancy in transgenic mice," *Nature*, 318(6046):533-538, Dec. 12-18, 1985.
Adjei and Garren, "Pulmonary delivery of peptide drugs: effect of particle size on bioavailability of leuprolide acetate in healthy male volunteers," *Pharm Res.*, 7(6):565-569, Jun. 1990.
Adjei et al., "Bioavailability of leuprolide following intratracheal administration to beagle dogs," *Int. J. Pharmaceutics*, 63(1-2):135-144, Jun. 11, 1990.
Alexander et al., "Expression of the c-myc oncogene under control of an immunoglobulin enhancer in E mu-myc transgenic mice," *Mol Cell Biol.*, 7(4): 1436-1444, Apr. 1987.
Altmeyer et al., "Tumor-specific cell surface expression of the-KDEL containing, endoplasmic reticular heat shock protein gp96," *Int J Cancer.*, 69(4):340-349, Aug. 22, 1996.
Ames, "Identifying environmental chemicals causing mutations and cancer," *Science*, 204(4393):587-593, May 11, 1979.
Ausubel et al., ed., 1999, Short Protocols in Molecular Biology (4th Edition, John Wiley & Sons. Inc., New York) Unit 10.11, pp. 10-86 to 10-88.
Banchereau and Steinman, "Dendritic cells and the control of immunity," *Nature*, 1988, 392(6673):245-252, Mar. 19, 1998.
Bardwell and Craig, "Major heat shock gene of *Drosophila* and the *Escherichia coli* heat-inducible dnaK gene are homologous," *Proc Natl Acad Sci U S A.*, 81(3):848-852, Feb. 1984.
Barrios et al., "Mycobacterial heat-shock proteins as carrier molecules. II: The use of the 70-kDa mycobacterial heat-shock protein as carrier for conjugated vaccines can circumvent the need for adjuvants and Bacillus Calmette Guérin priming," *Eur J Immunol.*, 22(6):1365-1372, Jun. 1992.
Bartlett, "Effect of host immunity on the antigenic strength of primary tumors," *J Natl Cancer Inst.*, 49(2):493-504, Aug. 1972.

(56) References Cited

OTHER PUBLICATIONS

Belli et al., "Vaccination of metastatic melanoma patients with autologous tumor-derived heat shock protein gp96-peptide complexes: clinical and immunologic findings," *J Clin Oncol.*, 20(20):4169-4180, Oct. 15, 2002.

Beltràn and Colomer, "Does HER-2 status predict only a decreased response to hormone therapy in advanced breast cancer, or does it also predict the extent of metastatic disease?" *J Clin Oncol.*, 20(23):4605-4610, Dec. 1, 2002.

Belyaysky et al., "PCR-based cDNA library construction: general cDNA libraries at the level of a few cells," *Nucleic Acids Res.*, 17(8):2919-2932, Apr. 25, 1989.

Benhamou and Siraganian, "Protein-tyrosine phosphorylation: an essential component of Fc epsilon RI signaling," *Immunol Today*, 13(6):195-197, Jun. 1992.

Benoist and Chambon, "In vivo sequence requirements of the SV40 early promotor region," *Nature*, 290(5804):304-310, Mar. 26, 1981.

Benton and Davis, "Screening lambdagt recombinant clones by hybridization to single plaques in situ," Science, 196(4286):180-182, Apr. 8, 1977.

Bernard et al., 1981, "Plasmacytomas with more than one immunoglobulin kappa mRNA: implications for allelic exclusion", Proc Natl Acad Sci U S A., 78(9):5812-5816, Sep. 1981.

Bernhardt et al., "Telomerase peptide vaccination of patients with non-resectable pancreatic cancer: A dose escalating phase I/II study," *Br J Cancer.*, 95(11):1474-1482, Epub Oct. 24, 2006.

Bitter et al., "[33] Expression and secretion 1987 vectors for yeast," *Methods Enzymol.*, 153:516-544, 1987.

Bitter, "[70] Heterologous gene expression in yeast," *Methods Enzymol.*, 152: 673-684, 1987.

Blachere et al., "Heat shock protein vaccines against cancer," *J Immunother Emphasis Tumor Immunol.*, 14(4):352-356, Nov. 1993.

Blachere et al., "Immunization with GP96 heat shock proteins isolated from tumors or influenza virus infected cells elicits MHC-restricted, antigen-specific cytotoxic T lymphocytes against the corresponding cells/antigens" *J. Cell. Biochem.*, 53(S17D):124, Abstract NZ 502, Mar. 13, 1993.

Boesen et al., "Circumvention of chemotherapy-induced myelosuppression by transfer of the mdrl gene," *Biotherapy*, 6(4):291-302, 1994.

Boon et al., "Tumor antigens recognized by T lymphocytes," *Annu. Rev. Immunol.*, 12:337-365, Apr. 1994.

Bowen et al., "Structure and expression of murine CD30 and its role in cytokine production," *J Immunol.*, 156(2):442-449, Jan. 15, 1996.

Braquet et al., "Effect of endothelin-1 on blood pressure and bronchopulmonary system of the guinea pig," *J Cardiovasc Pharmacol.*, 13(Suppl. 5):S143-S146, 1989.

Brinster et al., "Regulation of metallothionein—thymidine kinase fusion plasmids injected into mouse eggs," *Nature*, 296(5852):39-42, Mar. 4, 1982.

Bumol et al., "Characterization of the human tumor and normal tissue reactivity of the KS1/4 monoclonal antibody," *Hybridoma*, 7(4):407-415, Aug. 1988.

Cappechi, "High efficiency transformation by direct microinjection of DNA into cultured mammalian cells," *Cell*, 22(2 Pt 2):479-488, Nov. 1980.

Carswell et al., "Immunogenic properties of reticulum cell sarcomas of SJL/J mice," *J Natl Cancer Inst.*, 44(6):1281-1288, Jun. 1970.

Catalona et al., "Detection of organ-confined prostate cancer is increased through prostate-specific antigen-based screening," *JAMA*, 270(8):948-954, Aug. 25, 1993.

Chang et al., "Synergistic effect of 4-hydroperoxycyclophosphamide and etoposide on a human promyelocytic leukemia cell line (HL-60) demonstrated by computer analysis," *Cancer Res.* 45:2434-2439, Jun. 1985.

Chen et al., "Expression of ssDNA in mammalian cells," *Biotechniques*, 34(1):167-71, Jan. 2003.

Choulika et al., "Transfer of single gene-containing long terminal repeats into the genome of mammalian cells by a retroviral vector carrying the cre gene and the loxP site," *J Virol.*, 70(3):1792-1798, Mar. 1996.

Cline, "Perspectives for gene therapy: inserting new genetic information into mammalian cells by physical techniques and viral vectors," *Pharmac. Ther.*, 29(1):69-92, 1985.

Clontech catalog 1995-1996, Table of Contents, and pp. 137-138.

Clontech catalog 1997-1998, p. 146, 147, 149, 150, 151, 153,.

Clontech catalog, "Talon Metal Affinity Resin", 1997-1998, 2 pages.

Colbère-Garapin et al., "A new dominant hybrid selective marker for higher eukaryotic cells," *J Mol Biol.*, 150(1):1-14, Jul. 25, 1981.

Colombo et al., "Direct in vivo DC targeting by cellular vaccines engineered to express OX-4UGM-CSF or soluble HSP70", 93rd Annual Meeting of the American Association of Cancer Research. Mar. 2002, Abstract #3370.

Cotten et al., "[42] Receptor-mediated transport of DNA into eukaryotic cells," *Methods Enzymol.*, 217:618-644, 1993.

Craig, "Chaperones: helpers along the pathways to protein folding" *Science*, 260(5116):1902-1903, Jun. 25, 1993.

Curiel et al., "Adenovirus enhancement of transferrin-polylysine-mediated gene delivery," *Proc Natl Acad Sci U S A.*, 88(19):8850-8854, Oct. 1, 1991.

Current Protocols in Molecular Biology, vol. 3, Nov. 1988, 1 page [synopsis].

Davidson et al., "A model system for in vivo gene transfer into the central nervous system using an adenoviral vector," *Nat Genet.*, 3(3):219-223, Mar. 1993.

Davis et al., "Direct gene transfer into skeletal muscle in vivo: factors affecting efficiency of transfer and stability of expression," *Hum Gene Ther.*, 4(2):151-159, Apr. 1993.

de Boer et al., "The tac promoter: a functional hybrid derived from the trp and lac promoters," *Proc Natl Acad Sci U S A.*, 80(1):21-25, Jan. 1983.

Debs et al., "Lung-specific delivery of cytokines induces sustained pulmonary and systemic immunomodulation in rats," *J. Immunol.*, 140(10):3482-3488, May 15, 1988.

Demotz et al, "Characterization of a naturally processed MHC class II-restricted T-cell determinant of hen egg lysozyme," *Nature*, 342(6250):682-684, Dec. 7, 1989.

di Guan et al., "Vectors that facilitate the expression and purification of foreign peptides in *Escherichia coli* by fusion to maltose-binding protein," *Gene*, 67(1):21-30, Jul. 15, 1988.

Dolby et al., "Cloning and partial nucleotide sequence of human immunoglobulin mu chain cDNA from B cells and mouse-human hybridomas," *Proc Natl Acad Sci U S A.*, 77(10):6027-6031, Oct. 1980.

Dols et al., "Vaccination of women with metastatic breast cancer, using a costimulatory gene (CD80)-modified, HLA-A2-matched, allogeneic, breast cancer cell line: clinical and immunological results," *Hum Gene Ther.*, 14(11):1117-1123, Jul. 20, 2003.

Domec et al., "cDNA library construction from small amunts of unfractionated RNA: association of cDNA synthesis with polymerase chain reaction amplification," *Anal Biochem.*, 188(2):422-426, Aug. 1, 1990.

Ebert et al., "Characterization of an immunosuppressive factor derived from colon cancer cells," *J Immunol.*, 138(7):2161-2168, Apr. 1, 1987.

Elliott et al., "Antigen presentation. Naturally processed peptides," *Nature*, 348(6298):195-197, Nov. 15, 1990.

Estin et al., "Transfected mouse melanoma lines that express various levels of human melanoma-associated antigen p97," *J Natl Cancer Inst.*, 81(6):445-448, Mar. 15, 1989.

Falk et al., "Allele-specific motifs revealed by sequencing of self-peptides eluted from MHC molecules" Nature, 351(6324):290-296, May 23, 1991.

Falk et al., "Cellular peptide composition governed by major histocompatibility complex class I molecules," *Nature*, 348(6298):248-251, Nov. 15, 1990.

Falkner and Zachau, "Expression of mouse immunoglobulin genes in monkey cells," *Nature*, 298(5871):286-288, Jul. 15, 1982.

(56) References Cited

OTHER PUBLICATIONS

Feldweg and Srivastava, "Evidence for biochemical heterogeneity of gp96 heat shock protein/tumor rejection antigen," *J Cell Biochem.*, Suppl. 17D:108, Abstract NZ 206, 1993.

Feldweg and Srivastava, "Molecular heterogeneity of tumor rejection antigen/heat shock protein GP96," *Int J Cancer.*, 63(2):310-314, Oct. 9, 1995.

Flynn, et al., "Peptide binding and release by proteins implicated as catalysts of protein assembly," *Science*, 245(4916):385-390, Jul. 28, 1989.

Flynn, et al., "Peptide-binding specificity of the molecular chaperone BiP," Nature, 353(6346):726-730, Oct. 24, 1991.

Fong and Engleman, "Dendritic cells 2000 in cancer immunotherapy," *Annu Rev Immunol.*, 18:245-273, 2000.

Franklin, "Making vaccines fit the cancer," *New Scientist*, 140:17, 1993.

Geller and Freese, "Infection of cultured central nervous system neurons with a defective herpes simplex virus 1 vector results in stable expression of *Escherichia coli* beta-galactosidase," *Proc Natl Acad Sci U S A*,;87(3):1149-1153, Feb. 1990.

Geller et al., "An HSV-1 vector expressing tyrosine hydroxylase causes production and release of L-dopa from cultured rat striatal cells," *J. Neurochem*, 64:487-496, Feb. 1995.

Geller et al., "Long-term increases in neurotransmitter release from neuronal cells expressing a constitutively active adenylate cyclase from a herpes simplex virus type 1 vector," *Proc Natl Acad Sci U S A*, 90(16):7603-7607, Aug. 15, 1993.

Genebank Accession M16370, GI:200582, "Mouse polymorphic tumor rejection antigen (gp96), 5' end," Apr. 27, 1993, 1 page.

Genebank Accession M19645, GI:183644, "Human 78 kdalton glucose-regulated protein (GRP78) gene, complete cds," Nov. 8, 1994, 3 pages.

Genebank Accession M24743, GI:188527, "Human MHC class III heat shock protein HSP70-1 gene, 5' end," Jan. 7, 1995, 1 page.

Genebank Accession M35021, GI:194022, "Mouse heat shock protein 70.1 (hsp70.1) gene, complete cds," Mar. 26, 1994, 2 pages.

Genebank Accession U16277, GI:829364, "Mus musculus 78 kDa glucose-regulated protein (grp78) gene, promoter region and partial cds," Sep. 29, 1995, 2 pages.

Genebank Accession X15187, GI:37260, "Human tral mRNA for human homologue of murine tumor rejection antigen gp96," Mar. 31, 1995, 2 pages.

Gething and Sambrook, "Protein folding in the cell," *Nature*, 355(6355):33-45, Jan. 2, 1992.

Gething et al., "Expression of wild-type and mutant forms of influenza hemagglutinin: the role of folding in intracellular transport," *Cell*, 46(6):939-50, Sep. 12, 1986.

Glasebrook and Fitch, "Alloreactive cloned T cell lines. I. Interactions between cloned amplifier and cytolytic T cell lines," *J Exp Med.*, 151(4):876-895, Apr. 1, 1980.

Gorman, "Mammalian cell expression," *Curr Opin Biotechnol.*, 1(1):36-47, Oct. 1990.

Gough et al., "Molecular cloning of seven mouse immunoglobulin kappa chain messenger ribonucleic acids," *Biochemistry*, 19(12):2702-2710, Jun. 10, 1980.

Graham et al., "Characteristics of a human cell line transformed by DNA from human adenovirus type 5," *J Gen Virol.*, 36(1):59-74, Jul. 1977.

Grosschedl et al., "Introduction of a mu immunoglobulin gene into the mouse germ line: specific expression in lymphoid cells and synthesis of functional antibody," *Cell*, 38(3):647-658, Oct. 1984.

Grossman and Wilson, "Retroviruses: delivery vehicle to the liver," *Curr Opin Genet Dev.*, 3(1):110-114, Feb. 1993.

Grunstein and Hogness, "Colony hybridization: a method for the isolation of cloned DNAs that contain a specific gene," *Proc Natl Acad Sci U S A*, 72(10):3961-3965, Oct. 1975.

Haas and Meo, "cDNA cloning of the immunoglobulin heavy chain binding protein," *Proc Natl Acad Sci U S A*, 85(7):2250-2254, Apr. 1988.

Haas and Wabl, "Immunoglobulin heavy chain binding protein," *Nature*, 306(5941):387-389, Nov. 24-30, 1983.

Hamer et al., "SV40 recombinants carrying rabbit beta-globin gene coding sequences," *Cell*, 17(3):725-735, Jul. 1979.

Hanahan, "Heritable formation of pancreatic beta-cell tumours in transgenic mice expressing recombinant insulin/simian virus 40 oncogenes," *Nature*, 315(6015):115-22, May 9-15, 1985.

Hauser et al., "Secretory heat-shock protein as a dendritic cell-targeting molecule: a new strategy to enhance the potency of genetic vaccines," *Gene Ther.*, 11:924-932. Jun. 2004.

Healthcare Professionals-Results of Past Trials, Retrieved from Website of Antigenics Inc. on the Internet at: <URL: www.antiqenics.com/p healthcare03.html> on Oct. 19, 2001, 10 pages.

Heike et al., "Protective cellular immunity against a spontaneous mammary carcinoma from ras transgenic mice," *Immunobiology*, 190(4-5):411-423, Jun. 1994.

Henttu and Vihko, "cDNA coding for the entire human prostate specific antigen shows high homologies to the human tissue kallikrein genes," *Biochem Biophys Res Commun.* 160(2):903-910, Apr. 28, 1989.

Hickey et al., "Sequence and regulation of a gene encoding a human 89-kilodalton heat shock protein," *Mol Cell Biol.*, 9(6):2615-2626, Jun. 1989.

Hickey, "Basic principles of immunological surveillance of the normal central nervous system," *Glia*, 36(2):118-124, Nov. 2001.

Hill et al., "Mutagenesis with degenerate oligonucleotides: an efficient method for saturating a defined DNA region with base pair substitutions," *Methods Enzymol.*, 155:558-568, 1987.

Ho et al., "Site-directed mutagenesis by overlap extension using the polymerase chain reaction," *Gene*, 77(1):51-59, Apr. 15, 1989.

Holmskov et al., "Collectins: collagenous C-type lectins of the innate immune defense system," *Immunol Today*, 15(2):67-74, Feb. 1994.

Hoover et al., "Adjuvant active specific immunotherapy for human colorectal cancer: 6.5-year median follow-up of a phase III prospectively randomized trial," *J Clin Oncol.*, 11(3):390-399, Mar. 1993.

Hunt and Morimoto, "Conserved features of eukaryotic hsp70 genes revealed by comparison with the nucleotide sequence of human hsp70," *Proc Natl Acad Sci U S A*, 82(19):6455-6459, Oct. 1985.

Hutchison et al., "Mutagenesis at a specific position in a DNA sequence," *J Biol Chem.*, 253(18):6551-6560, Sep. 25, 1978.

Israeli et al., "Molecular cloning of a complementary DNA encoding a prostate-specific membrane antigen," *Cancer Res.*, 53(2):227-230, Jan. 15, 1993.

Jardetzky et al., "Identification of self peptides bound to purified HLA-B27," *Nature*, 353(6342):326-329, Sep. 26, 1991.

Jindal et al., "Primary structure of a human mitochondrial protein homologous to the bacterial and plant chaperonins and to the 65-kilodalton mycobacterial antigen," *Mol Cell Biol.*, 9(5):2279-2283, May 1989.

Kaplitt et al., "Long-term gene expression and phenotypic correction using adeno-associated virus vectors in the mammalian brain," *Nat Genet.*, 8(2):148-154, Oct. 1994.

Karasuyama and Melchers, "Establishment of mouse cell lines which constitutively secrete large quantities of interleukin 2, 3, 4 or 5, using modified cDNA expression vectors," *Eur J Immunol.*, 18(1):97-104, Jan. 1988.

Kelsey et al., "Species- and tissue-specific expression of human alpha 1-antitrypsin in transgenic mice," *Genes Dev.*, 1(2):161-171, Apr. 1987.

Kimmel and Berger, "[32] Preparation of cDNA and the generation of cDNA libraries: Overview" *Methods Enzymol*, 152:307-316, 1987.

Klein et al., "Demonstration of resistance against methylcholanthrene-induced sarcomas in the primary autochthonous host," *Cancer Res.*, 20:1561-1572, Dec. 1960.

Kiernan et al., "Optimal conditions for freezing CHO-S and HEK293-EBNA cell lines: influence of Me2S0, freeze density, and PEI-mediated transfection on revitalization and growth of cells, and expression of recombinant protein," *Biotechnology and Bioengineering*, 100(5):911-922, Aug. 1, 2008.

Koff et al., Replicating viral vectors as HIV vaccines: Summary Report from IAVI Sponsored Satellite Symposium, International AIDS Society Conference, Jul. 22, 2007, *Biologicals*, 36(5):277-286.

(56) References Cited

OTHER PUBLICATIONS

Kollias et al., "Regulated expression of human A gamma-, beta-, and hybrid gamma beta-globin genes in transgenic mice: manipulation of the developmental expression pattersn," *Cell*, 46(1):89-94, Jul. 4, 1986.
Kos, "Regulation of adaptive immunity by natural killer cells," *Immunol Res.*, 17(3):303-312, 1998.
Kripke, "Antigenicity of murine skin tumors induced by ultraviolet light," *J Natl Cancer Inst.*, 53(5):1333-1336, Nov. 1974.
Krumlauf et al., "Developmental regulation of alpha-fetoprotein genes in transgenic mice," *Mol Cell Biol.*, 5(7):1639-1648, Jul. 1985.
Lai et al., "Quantitation and intracellular localization of the 85K heat shock protein by using monoclonal and polyclonal antibodies," *Mol Cell Biol.*, 4(12):2802-2810, Dec. 1984.
Langone, "Use of labeled protein A in quantitative immunochemical analysis of antigens and antibodies," *J Immunol Methods*, 51(1):3-22, 1982.
Lanzavecchia, "Identifying strategies for immune intervention," *Science*, 260(5110):937-944, May 14, 1993.
Leder et al., "Consequences of widespread deregulation of the c-myc gene in transgenic mice: multiple neoplasms and normal development," *Cell*, 45(4):485-495, May 23, 1986.
Lee et al., "The genomic organization of the CD28 gene. Implications for the regulation of CD28 mRNA expression and heterogeneity," *J Immunol.*, 145(1):344-352, Jul. 1, 1990.
Levinson et al., "Metal binding drugs induce synthesis of four proteins in normal cells," Biol Trace Elem Res., 1(1):15-23, Mar. 1979.
Lévy et al., "ATP is required for in vitro assembly of MHC class I antigens but not for transfer of peptides across the ER membrane," *Cell*, 67(2):265-274, Oct. 18, 1991.
Liu, "Treg suppress CTL responses upon immunization with HSP gp96," *Eur J Immunol.*, 39(11):3110-3120, Nov. 2009.
Loeffler and Behr, "[41] Gene transfer into primary and established mammalian cell lines with lipopolyamine-coated DNA," *Methods Enzymol.*, 217:599-618, 1993.
Logan and Shenk, "Adenovirus tripartite leader sequence enhances translation of mRNAs late after infection," *Proc Natl Acad Sci U S A.*, 81(12):3655-3659, Jun. 1984.
Lowy et al., "Isolation of transforming DNA: cloning the hamster aprt gene," *Cell*, 22(3):817-823, Dec. 1980.
Luescher et al., "Specific binding of antigenic peptides to cell-associated MHC class I molecules," *Nature*, 351(6321):72-74, May 2, 1991.
Lussow et al., "Mycobacterial heat-shock proteins as carrier molecules," *Eur J Immunol.*, 21(10):2297-2302, Oct. 1991.
MacDonald et al., "Expression of the pancreatic elastase I gene in transgenic mice," *Hepatology*, 7(1 Suppl):42S-51S, Jan.-Feb. 1987.
Machamer et al., "Heavy chain binding protein recognizes incompletely disulfide-bonded forms of vesicular stomatitis virus G protein," *J Biol Chem.*, 265(12):6879-6883, Apr. 25, 1990.
Mackett et al., "General method for production and selection of infectious vaccinia virus recombinants expressing foreign genes," *J Virol.*, 49(3):857-864, Mar. 1984.
Mackett et al., "Vaccinia virus: a selectable eukaryotic cloning and expression vector," *Proc Natl Acad Sci U S A.*, 79(23):7415-7419, Dec. 1982.
Madden et al., "The structure of HLA-B27 reveals nonamer self-peptides bound in an extended conformation," *Nature*, 353(6342):321-325, Sep. 26, 1991.
Magram et al., "Developmental regulation of a cloned adult beta-globin gene in transgenic mice," *Nature*, 315(6017):338-340, May 23-29, 1985.
Maki et al., "Mapping of the genes for human endoplasmic reticular heat shock protein gp96/grp94," *Somat Cell Mol Genet.*, 19(1):73-81, Jan. 1993.
Makrides, "Strategies for achieving high-level expression of genes Escherichia coli," *Microbiol Rev.*, 60(3):512-538, Sep. 1996.

Massarelli et al., "A retrospective analysis of the outcome of patients who have received two prior chemotherapy regimens including platinum and docetaxel for recurrent non-small-cell lung cancer," *Lung Cancer*, 39(1): 55-61, 2003.
Mather, "Establishment and characterization of two distinct mouse testicular epithelial cell lines," *Biol. Reprod.*, 23:243-251, Aug. 1980.
Mazzaferro et al., "Vaccination with Autologous Tumor-derived Heat-Shock Protein Gp96 after Liver Resection for Metastatic Colorectal Cancer," *Clin Cancer Res.*, 9:3235-3245, Aug. 2003.
McCall et al, "Biotherapy: A new dimension 1989 in cancer treatment," *Nature Biotechnology* 7:231-240, 1989.
McCluskie et al., "Route and method of delivery of DNA vaccine influence immune responses in mice and non-human primates," *Mol Med.*, 5(5):287-300, May 1999.
McLaughlin et al., "Adeno-associated virus general transduction vectors: analysis of proviral structures," *J Virol.*, 62(6):1963-1973, Jun. 1988.
Ménoret et al., "Co-segregation of tumor immunogenicity with expression of inducible but not constitutive hsp70 in rat colon carcinomas," *J Immunol.*, 155(2):740-747, Jul. 15, 1995.
Merrifield, "Solid Phase Peptide Synthesis. I. The Synthesis of a Tetrapeptide," *J Am Chem Soc.*, 85(14): 2149-2154, Jul. 1, 1963.
Mizoguchi et al., "Alterations in signal transduction molecules in T lymphocytes from tumor-bearing mice," *Science*, 258(5089):1795-1798, Dec. 11, 1992.
Morgenstern and Land, "Advanced mammalian gene transfer: high titre retroviral vectors with multiple drug selection markers and a complementary helper-free packaging cell line," *Nucleic Acids Res.*, 18(12):3587-3596, Jun. 25, 1990.
Morrison and Oi, "Transfer and expression of immunoglobulin genes," *Annu Rev Immunol.*, 2:239-256, 1984.
Mosmann and Sad, "The expanding universe of T-cell subsets: Thl, Th2 and more," *Immunol Today*, 17(3):138-146, Mar. 1996.
Mulligan and Berg, "Selection for animal cells that express the *Escherichia coli* gene coding for xanthine-guanine phosphoribosyltransferase," *Proc Natl Acad Sci U S A*, 78(4):2072-2076, Apr. 1981.
Munro and Pelham, "A C-terminal signal prevents secretion of luminal ER proteins," *Cell*, 48(5):899-907, Mar. 13, 1987.
Munro and Pelham, "An Hsp70-like protein in the ER: identity with the 78 kd glucose-regulated protein and immunoglobulin heavy chain binding protein," *Cell*, 46(2):291-300, Jul. 18, 1986.
Natali et al , "Immunohistochemical detection of antigen in human primary and metastatic melanomas by the monoclonal antibody 140.240 and its possible prognostic significance," *Cancer*, 59(1):55-63, Jan. 1, 1987.
Neelapu et al., "Vaccine-induced tumor-specific immunity despite severe B-cell depletion in mantle cell lymphoma," Nat Med., 11(9):986-991. Epub Aug. 21, 2005.
Nielsen and Krogh, "Prediction of signal peptides and signal anchors by a hidden Markov model," *Proc Int Conf Intell Syst Mol Biol.*, 6:122-130, 1998.
Nielsen et al., "Identification of prokaryotic and eukaryotic signal peptides and prediction of their cleavage sites," *Protein Eng.*, 10(1):1-6, Jan. 1997.
O'Garra, "Cytokines induce the development of functionally heterogeneous T helper cell subsets," *Immunity*, 8(3):275-283, Mar. 1998.
O'Hare et al., "Transformation of mouse fibroblasts to methotrexate resistance by a recombinant plasmid expressing a prokaryotic reductase," *Proc Natl Acad Sci U S A.*, 78(3):1527-1531, Mar. 1981.
Oizumi et al., "Investigation of the antitumor effect of tumor cell-produced gp96 in the absence of B cells," *The Japan Lung Cancer Society*, 46(5):536, Abstract P-41, Oct. 2006.
Palladino et al., "Expression of a shared tumor-specific antigen by two chemically induced BALB/c sarcomas," *Cancer Res.*, 47(19):5074-5079, Oct. 1, 1987.
Panicali and Paoletti, "Construction of poxviruses as cloning vectors: insertion of the thymidine kinase gene from herpes simplex virus into the DNA of infectious vaccinia virus," 79(16):4927-4931, Aug. 1982.
Perrin et al., "Astrocytoma infiltrating lymphocytes include major T cell clonal expansions confined to the CD8 subset," *Int Immunol.*, 11(8):1337-1350, Aug. 1999.

(56) References Cited

OTHER PUBLICATIONS

Pinkert et al., "An albumin enhancer located 10 kb upstream functions along with its promoter to direct efficient, liver-specific expression in transgenic mice," *Genes Dev.*, 1(3):268-276, May 1987.
Prehn and Main, "Immunity to methylcholanthrene-induced sarcomas," *J Natl Cancer Inst.*, 18(6):769-778, Jun. 1957.
Quantin et al., "Adenovirus as an expression vector in muscle cells in vivo," *Proc natl Acad Sci U S A*, 89(7):2581-2584, Apr. 1, 1992.
Raez et al., "Allogeneic vaccination with a B7.1 HLA-A gene-modified adenocarcinoma cell line in patients with advanced non-small-cell lung cancer," *J Clin Oncol.*, 22(14):2800-2807, Jul. 15, 2004.
Rice and Baltimore, "Regulated expression of an immunoglobulin kappa gene introduced into a mouse lymphoid cell line," *Proc Natl Acad Sci U S A*, 79(24):7862-7865, Dec. 1982.
Rothman, "Polypeptide chain binding proteins: catalysts of protein folding and related processes in cells," *Cell*, 59(4):591-601, Nov. 1989.
Rotzschke et al., "Isolation and analysis of naturally processed viral peptides as recognized by cytotoxic T cells" *Nature*, 348(6298):252-254, Nov. 15, 1990.
Roy et al., "IL-12 treatment of endogenously arising murine brain tumors," *J Immunol.*, 165(12):7293-7299, Dec. 15, 2000.
Rudensky et al., "Sequence analysis of peptides bound to MHC class II molecules," *Nature*, 353(6345):622-627, Oct. 17, 1991.
Salk et al., "A strategy for prophylactic vaccination against HIV," *Science*, 260(5112):1270-1272, May 28, 1993.
Schneider et al., "Abnormal oxidative metabolism of estradiol in women with breast cancer," *Proc Natl Acad Sci U S A.*, 79(9):3047-3051, May 1982.
Schumacher et al., "Peptide selection by MHC class I molecules," *Nature*, 350(6320):703-706, Apr. 25, 1991.
Shankarappa et al., "Introduction of multiple restriction enzyme sites by in vitro mutagenesis using the polymerase chain reaction," *PCR Methods Appl.*, 1(4):277-278, May 1992.
Shilo and Weinberg, "DNA sequences homologous to vertebrate oncogenes are conserved in *Drosophila melanogaster*," *Proc Natl Acad Sci U S A*, 78(11):6789-6792, Nov. 1981.
Shiue et al., "A second chain of human CD8 is expressed on peripheral blood lymphocytes," *J Exp Med.*, 168(6):1993-2005, Dec. 1, 1988.
Sigma Life Science Research Immunochemicals 1998 catalog and price list © 1997, Table of Contents and pp. 144-146.
Sjöbring et al., "*Streptococcal* protein G. Gene structure and protein binding properties," *J Biol Chem.*, 266(1):399-405, Jan. 5, 1991.
Smith et al., "Molecular Engineering of the Autographa californica Nuclear Polyhedrosis Virus Genome: Deletion Mutation Within the Polyhedrin Gene," *J. Virol.*, 46(2):584-593, May 1983.
Smith et al., "Pulmonary deposition and clearance of aerosolized alpha-1-proteinase inhibitor administered to dogs and to sheep," *J Clin Invest.*, 84(4):1145-1154, Oct. 1989.
Srivastava and Das, "The serologically unique cell surface antigen of Zajdela ascitic hepatoma is also its tumor-associated transplantation antigen," *Int J Cancer.*, 33(3):417-422, Mar. 15, 1984.
Srivastava and Maki, "Stress-induced proteins in immune response to cancer," *Curr Top Microbiol Immunol.*, 167:109-123, 1991.
Srivastava and Old, "Individually distinct transplantation antigens of chemically induced mouse tumors," *Immunol Today.*, 9(3):78-83, Mar. 1988.
Srivastava et al., "5'-structural analysis of genes encoding polymorphic antigens of chemically induced tumors," *Proc Natl Acad Sci U S A*, 84(11):3807-3811, Jun. 1987.
Srivastava et al., "Evidence for peptide-chaperoning by the endoplasmic reticular heat shock protein GP96: Implications for vaccination against cancer and infectious diseases" *J. Cell. Biochem.* Supp. 17D: 94 Abstract NZ 014, 1993.
Srivastava, "Peptide-binding heat shock proteins in the endoplasmic reticulum: role in immune response to cancer an in antigen presentation," *Adv Cancer Res.*, 62:153-177, 1993.
Srivastava, "Protein tumor antigens," *Curr Opin Immunol.*, 3(5):654-658, Oct. 1991.
Staveley-O'Carroll et al., "Induction of antigen-specific T cell anergy: An early event in the course of tumor progression," *Proc Natl Acad Sci U S A.*, 95(3):1178-1183, Feb. 3, 1998.
Stratford-Perricaudet et al., "Widespread long-term gene transfer to mouse skeletal muscles and heart," *J Clin Invest.*, 90(2):626-630, Aug. 1992.
Strbo et al., "Heat shock fusion protein gp96-Ig mediates strong CD8 CTL expansion in vivo," *Am J Reprod Immunol.*, 48(4):220-225, Oct. 2002.
Subbarao and Murphy, "A general overview of viral vaccine development," *Adv Exp Med Biol.*, 327:51-56, 1992.
Suto and Srivastava, "A mechanism for the specific immunogenicity of heat shock protein-chaperoned peptides," *Science*, 269(5230):1585-1588, Sep. 15, 1995.
Szybalska and Szybalski, "Genetics of human cell line. IV. DNA-mediated heritable transformation of a biochemical trait," *Proc Natl Acad Sci U S A*, 48:2026-2034, Dec. 15, 1962.
Tailor et al., "Nucleotide sequence of human prostatic acid phosphatase determined from a full-length cDNA clone," *Nucleic Acids Res.*, 18(16):4928, Aug. 25, 1990.
Tamura et al, "Immunotherapy of tumors with autologous tumor-derived heat shock protein preparations," *Science*, 278(5335):117-120, Oct. 3, 1997.
Taylor and Kingston, "Factor substitution in a human HSP70 gene promoter: TATA-dependent and TATA-independent interactions," *Mol Cell Biol.*, 10(1):165-175, Jan. 1990.
Thompson et al., "The CLUSTAL_X windows interface: flexible strategies for multiple sequence alignment aided by quality analysis tools," *Nucleic Acids Res.*, 25(24):4876-4882, Dec. 15, 1997.
Toes, "Peptide vaccination can lead to enhanced tumor growth through specific T-cell tolerance induction," *Proc Natl Acad Sci U S A.*, 93(15):7855-7860, Jul. 23, 1996.
Tollefsen et al., "DNA injection in combination with electroporation: a novel method for vaccination of farmed ruminants," *Scand J Immunol.* 57(3):229-238, Mar. 2003.
Udono and Srivastava, "Comparison of tumor-specific immunogenicities of stress-induced proteins gp96, hsp90, and hsp70," *J Immunol.*, 152(11):5398-5403, Jun. 1, 1994.
Udono and Srivastava, "Heat shock proteins HSP70, HSP90 an GP96 elicit tumor specific immunity to the tumors from which they are isolated" *J. Cell. Biochem.* Suppl. 17D: 1131 Abstract NZ 225, 1993.
Urlaub and Chasin, "Isolation of Chinese hamster cell mutants deficient in dihydrofolate reductase activity," *Proc Natl Acad Sci U S A.*, 77(7):4216-4220, Jul. 1980.
Vaage, "Nonvirus-associated antigens in virus-induced mouse mammary tumors," *Cancer Res.*, 28(12):2477-2483, Dec. 1968.
Van Doren and Gluzman, "Efficient transformation of human fibroblasts by adenovirus-simian virus 40 recombinants," *Mol Cell Biol.*, 4(8):1653-1656, Aug. 1984.
VanBogelen et al., "Induction of the heat shock regulon does not produce thermotolerance in *Escherichia coli*," *Genes Dev.*, 1(6):525-531, Aug. 1987.
Vijayasaradhi et al., "The melanoma antigen gp75 is the human homologue of the mouse b (brown) locus gene product," *J Exp Med.*, 171(4):1375-1380, Apr. 1, 1990.
Villa-Komaroff et al., "A bacterial clone synthesizing proinsulin," *Proc. Natl Acad Sci U S A.*, 75(8):3727-3731, Aug. 1978.
von Heijne, "Signal sequences. The limits of variation," *J Mol Biol.*, 184(1):99-105, Jul. 5, 1985.
Wagner et al., "Nucleotide sequence of the thymidine kinase gene of herpes simplex virus type 1," *Proc Natl Acad Sci U S A.*, 78(3):1441-1445, Mar. 1981.
Welch and Feramisco, "Rapid purification of mammalian 70,000-dalton stress proteins: affinity of the proteins for nucleotides," *Mol Cell Biol.*, 5(6):1229-1237, Jun. 1985.
Welch and Suhan, "Morphological study of the mammalian stress response: characterization of changes in cytoplasmic organelles, cytoskeleton, and nucleoli, and appearance of intranuclear actin filaments in rat fibroblasts after heat-shock treatment," *J Cell Biol.*, 101(4):1198-1211, Oct. 1985.
Welch, "How cells respond to stress," *Sci Am.*, 268(5):56-64, May 1993.

(56) References Cited

OTHER PUBLICATIONS

Wigler et al., "Transformation of mammalian cells with an amplifiable dominant-acting gene," *Proc Natl Acad Sci U S A*. 77(6):3567-3570, Jun. 1980.
William et al., "Revisiting stage IIIB and IV non-small cell lung cancer: analysis of the surveillance, epidemiology, and end results data," *Chest*, 136(3):701-709, Epub Mar. 24, 2009.
Williams et al., "Correlation between the induction of heat shock protein 70 and enhanced viral reactivation in mammalian cells treated with ultraviolet light and heat shock," *Cancer Res.*, 49(10):2735-2742, May 15, 1989.
Wolff et al., "Expression of retrovirally transduced genes in primary cultures of adult rat hepatocytes," *Proc Natl Acad Sci U S A*, 84(10):3344-3348, May 1987.
Yamazaki et al., "Application of secreted gp96 fusion protein (gp96-Ig) to immunogene therapy and cancer prevention," *The Japan Lung Cancer Society*, 40(5):388, Abstract B-29, Sep. 2000, 3 pages.
Yamazaki et al., Basic study of immunogene therapy by secretor-type gp96 fusion proteins (gp96- Ig), *The Japan Lung Cancer Society*, 41(5):527, Abstract P-20, Sep. 2001, 3 pages.
Yamazaki et al., "Effective therapeutic anti-tumor immunity generated by tumors secreting gp96-lg in FN syngeneic immunocompetent mice", 93rd Annual Meeting of the American Association of Cancer Research. Mar. 2002. Abstract #4821, 3 pages.
Yamazaki et al., "gp96 engineered for secretion of tumor peptides and for vaccination against cancer" *J Allergy Clin Immunol*, vol. 99, No. 1 Pt. 2, p. S45, Abstract 187, Jan. 1997.
Yang et al., "Cellular and humoral immune responses to viral antigens create barriers to lung-directed gene therapy with recombinant adenoviruses," *J Virol.*, 69(4):2004-2015, Apr. 1995.
Yanling Zhang, Hui Zhang, ed., Vaccinology, Beijing, science press, Mar., 2004, Version 1, ISBN 7-03-011586-4, paragraph 3 on p. 339 to the last paragraph on p. 343, [English translation], 19 pages.
Yu et al., "Coexpression of different antigenic markers on moieties that bear CA 125 determinants," *Cancer Res.*, 51(2):468-475, Jan. 15, 1991.
European Search Report for Application No. EP09720311, dated Nov. 27, 2012, 6 pages.
European Search Report for Application No. EP14152006.4, dated Jun. 5, 2014, 10 pages.
International Preliminary Report on Patentability for PCT/US2009/001330, issued Sep. 7, 2010, 7 pages.
International Search Report and Written Opinion for PCT/US2009/001330, mailed Oct. 14, 2009, 8 pages.
Allison and Byars, "Immunological Adjuvants and Their Mode of Action," *Vaccines: New Approaches to Immunological Problems*, Ellis, ed., Butterworth-Heinemann, Boston, Chapter 19, pp. 431-449, Feb. 3, 1992.
Ashwood-Smith and Friedmann, "Lethal and chromosomal effects of freezing, thawing, storage time, and x-irradiation on mammalian cells preserved at -196 degrees in dimethyl sulfoxide," *Cryobiology*, 16(2):132-140, Apr. 1979.
Capece et al., "Targeting costimulatory molecules to improve antitumor immunity," *J. Biomed Biotechnol.*, vol. 2012 Article ID 926321, 17 pages, Epub Feb. 12, 2012.
Creelan, "Update on immune checkpoint inhibitors in lung cancer," *Cancer Control*, 21(1):80-89m Jan. 2014.
Dillman et al., "Clinical experience with autologous tumor cell lines for patient-specific vaccine therapy in metastatic melanoma," *Cancer Biother Radiopharm.*, 13(3):165-176, Jun. 1998.
Dunn et al., "Cancer immunoediting: from immunosurveillance to tumor escape," *Nat Immunol.*, 3(11):991-998, Nov. 2002.
Dunn et al., "The three Es of cancer immunoediting," *Annu Rev Immunol.*, 22:329-360, 2004.
GenBank Accession No. X15187, "*Homo sapiens* tral mRNA for human homologue of murine tumor rejection antigen gp96," Apr. 18, 2005, 2 pages.
Höckel and Vaupel, "Tumor hypoxia: definitions and current clinical, biologic, and molecular aspects," *J Natl Cancer Inst.*, 93(4):266-276, Feb. 21, 2001.

Hudrisier et al., "Cutting edge: CTLs rapidly capture membrane fragments from target cells in a TCR signaling-dependent manner," *J Immunol.*, 166(6):3645-3649, Mar. 15, 2001.
Hwang et al., "T cells can use either T cell receptor or CD28 receptors to absorb and internalize cell surface molecules derived from antigen-presenting cells," *J Exp Med.*, 191(7):1137-1148, Apr. 3, 2000.
Lorber et al., "I-A antigens on cloned alloreactive murine T lymphocytes are acquired passively," *J. Immunol.*, 128(6):2798-2803, Jun. 1982.
Maki et al., "Human homologue of murine tumor rejection antigen gp96: 5'-regulatory and coding regions and relationship to stress-induced proteins," *Proc Natl Acad Sci USA*, 87(15):5658-5562, Aug. 1990.
Minakata et al., "Hypoxia induces gefitinib resistance in non-small-cell lung cancer with both mutant and wild-type epidermal growth factor recptors," *Cancer Sci.*, 103(11):1946-1954, Epub Sep. 14, 2012.
Miraglia et al., "Effect of freezing on the in vivo recovery of irradiated red cells," *Transfusion*, 34(9):775-778, Sep. 1994.
Nakamura et al., "Cell contact-dependent immunosuppression by CD4(+)CD25(+) regulatory T cells is mediated by cell surface-bound transforming growth factor beta," *J. Exp. Med.*, 194(5):629-644, Sep. 3, 2001.
Pardoll, "The blockade of immune checkpoints in cancer immunotherapy," *Nat Rev Cancer.*, 12(4):252-264, Mar. 22, 2012.
Rabinovich et al., "Immunosuppressive strategies that are mediated by tumor cells," *Annu Rev Immunol.*, 25:267-296, 2007.
Raulet and Guerra, "Oncogenic stress sensed by the immune system: role of natural killer cell receptors," *Nat Rev Immunol.*, 9(8):568-580, Aug. 2009.
Sabzevari et al., "Acquisition of CD80 (B7-1) by T cells," *J. Immunol.*, 166(4):2505-2513, Feb. 15, 2001.
Schreiber and Podack, "Comparative combination cancer immunotherapy with vaccination, checkpoint inhibition and TNFRSF stimulation (VAC12P.1021)," *The Journal of Immunology*, May 1, 2014 vol. 192 (1 Supplement) 206.10.
Schreiber et al., "T cell costimulation by TNFR superfamily (TNFRSF)4 and TNFRSF25 in the context of vaccination," *J Immunol.*, 189(7):3311-3318, Sep. 5, 2012.
Schreiber et al., "Comparative combination cancer immunotherapy with vaccination, checkpoint inhibition and TNFRSF stimulation," [abstract]. In: Proceedings of the 105th Annual Meeting of the American Association for Cancer Research, San Diego, CA. Philadelphia (PA): AACR; *Cancer Res.*, 74(19 Suppl):Abstract 5029, 1 page Apr. 5-9, 2014.
Shankaran et al., "IFNgamma and lymphocytes prevent primary tumour development and shape tumour immunogenicity," *Nature*, 410(6832):1107-1111, Apr. 26, 2001.
Smyth et al., "Cancer immunosurveillance and immunoediting: the roles of immunity in suppressing tumor development and shaping tumor immunogenicity," *Adv Immunol.*, 90:1-50, 2006.
Szybalski and Szybalski, "Genetics of human cell line. IV. DNA-mediated heritable transformation of a biochemical trait," *Proc Natl Acad Sci USA*, 48:2026-2034, Dec. 15, 1962.
Taieb et al., "A novel dendritic cell subset involved in tumor immunosurveillance," *Nat Med.*, 12(2):214-219, Epub Jan. 29, 2006.
Takahashi et al., "Induction of CD8+ cytotoxic T cells by immunization with purified HIV-1 envelope protein in ISCOMs," *Nature*, 344(6269):873-875, Apr. 26, 1990.
Takasaki et al. "The expression of LFA-1, ICAM-1, CD80 and CD86 molecules in lupus patients: implication for immunotherapy," *Intern Med.*, 38(2):175-177, Feb. 1999.
Topalian et al., "Safety, activity, and immune correlates of anti—PD-1 antibody in cancer," *N Engl J Med.*, 366(26):2443-2454, Epub Jun. 2, 2012.
Unni et al., "Intrinsic sensor of oncogenic transformation induces a signal for innate immunosurveillance," *Proc Natl Acad Sci USA*, 105(5):1686-1691, Epub Jan. 25, 2008.
Veale et al., "Epidermal growth factor receptors in non-small cell lung cancer," *Br J Cancer*, 55(5):513-516, May 1987.

(56) References Cited

OTHER PUBLICATIONS

Warren and Chedid, "Future prospects for vaccine adjuvants," *Crit Rev Immunol.*, 8(2):83-101, 1988.
Woodlock et al., "Active specific immunotherapy for metastatic colorectal carcinoma: phase I study of an allogeneic cell vaccine plus low-dose interleukin-1 alpha," *J. Immunotherapy*, 22(3):251-259, May 1999.
Zijno et al., "Suitability of cryopreserved isolated lymphocytes for the analysis of micronuclei with the cytokinesis-block method," *Mutagenesis*, 22(5):311-315, Epub Jun. 4, 2007.

* cited by examiner

ALLOGENEIC CANCER CELL-BASED IMMUNOTHERAPY

CROSS-REFERENCE TO RELATED APPLICATION

This application is a continuation application of U.S. patent application Ser. No. 12/921,151, filed Sep. 3,2010, which claims priority from international patent application No. PCT/US2009/001330, filed Mar. 3,2009, which claims the benefit of U.S. provisional patent application No.61/033,425, filed Mar. 3, 2008, which is incorporated by reference.

FEDERALLY-SPONSORED RESEARCH OR DEVELOPMENT

The U.S. Government has certain rights in this invention as provided for in NIH contract CA039201 from the Department of Health and Human Services.

BACKGROUND OF THE INVENTION

This invention relates to improving cancer cell-based immunotherapy (e.g., immunization or vaccination) comprised of administration of allogeneic cancer cells secreting a modified heat shock protein to a human subject. It is improved by frequent administration of allogeneic cancer cells to the subject, depletion of B cells in the subject before and/or during the first or at least one administration of allogeneic cancer cells, or both.

WO 99/42121 disclosed a cell-based vaccine, wherein modified heat shock protein encoded by a transfected expression construct is secreted. The vaccine may be effective to treat or prevent cancer or infectious disease. One injection of recombinant cancer cells and two injections of recombinant cancer cells separated by two weeks were described. Autologous cancer cells were preferred. By contrast, the present invention uses allogeneic cancer cells.

WO 2005/030136 disclosed inhibiting a tumor by administering a lung cancer cell genetically modified to express CD80 and HLA. The cancer cell does not secrete a modified heat shock protein.

Cancer is typically treated by surgical resection of the tumor, radiation or drugs to kill cancer cells, or a combination thereof. The immune system can inhibit the multiplication and spread of cancer cells. They may escape immuno-logic surveillance, however, by being nonimmunogenic (e.g., non-small cell lung cancer), which blocks priming of the immune response to generate an effective response, or being immunogenic (e.g., melanoma) but blocking the effector phase of the immune response. Alternatively, blockade of priming could be due to the tumor secreting immunosuppressive mediators or tolerizing chemokines and/or stimulation of regulatory cells, tolerogenic antigen presenting cells, or myelosuppressor cells. Active immunotherapy by administering allogeneic cancer cells could circumvent blockade, and prime the innate and/or adaptive immune response. The induction and amplification of a tumor-specific $CD8^+$T-cell response would be especially desirable as evaluated by cytolysis of cancer cells or secretion of interferon gamma stimulated by cancer cells.

Raez et al. (J. Clin. Oncol. 22:2800-2807, 2004) described a phase I trial of an allogeneic cancer cell-based vaccine for non-small cell lung cancer in patients with advanced metastatic disease. Adenocarcinoma cell line AD100 was transfected to express CD80 and HLA-A1 or A2. Patients were immunized intradermally with $5 \times 10^7$ cells once every two weeks. Three immunizations represented one course of treatment. Unless a patient had no response to the initial immunization, up to three courses of treatment for a total of nine immunizations were administered. The promising results obtained using this cell-based vaccine might be improved by increasing the frequency of immunization and depleting B cells before and/or during at least one immunization.

Therefore, it is an objective of the present invention to provide improved immunotherapy (e.g., immunization or vaccination), which comprises administering allogeneic cancer cells secreting a modified heat shock protein to a human subject, by frequent administration, depletion of B cells before and/or during the initial or at least one administration, or both. Other advantages and improvements are described below or would be apparent from the disclosure herein.

SUMMARY OF THE INVENTION

The invention provides an improvement in allogeneic cancer cell-based immunotherapy for immunization and vaccination. The "treatment" may be therapeutic, prophylactic, or merely palliative.

A human subject is treated .by administering allogeneic cancer cells that secrete a modified heat shock protein (e.g., gp96). Here, "allogeneic" means that the administered cells and the treated subject differ by one or more major histocompatibility complex (MHC) molecules. Heat shock protein may be modified by removing a domain containing the retention signal for endoplasmic reticulum. Optionally, the domain may be replaced with one or more heavy chain constant region(s) of human or mouse immunoglobulin IgG1 or IgG2 (e.g., Fc domain). The modified heat shock protein is expressed from a nucleic acid within the cancer cell that was transfected by an expression vector or infected by a viral vector. The vector may be based on one or more regulatory signal(s) (e.g., transcription start and stop, slice donor and acceptor, polyadenylation, origin of replication) from bovine papilloma virus (BPV). The vector preferably does not contain the E5, E6 and E7 genes of BPV. Thus, the cancer cells can be considered "recombinant" because of the technology used to produce them.

Antigen (e.g., an epitope derived from neoantigen or tumor antigen of an allogeneic or syngeneic cancer cell) may induce an innate or adaptive immune response in the subject. In particular, induction and amplification of a $CD8^+$T-cell response is desirable. The $CD8^+$cell may kill cancer cells or secrete interferon gamma specifically.

Optionally, a cancer cell may be made allogeneic by expressing at least one MHC molecule, which is not expressed by the subject, from a nucleic acid within the cancer cell that was transfected by an expression vector or infected by a viral vector. The modified heat shock protein and HLA molecule may be at least partially encoded by the same vector or different vectors.

A human subject may be immunized several times with allogeneic cancer cells. The interval between two consecutive administrations of the cell-based immunogenic composition is less than two weeks. Another improvement may be B-cell depletion of the subject before and/or during at least one administration of the cell-based immunogenic composition.

Further objectives and advantages aspects of the invention will be apparent to a person skilled in the art from the following description of specific embodiments and the claims, and generalizations thereto.

DESCRIPTION OF SPECIFIC EMBODIMENTS OF THE INVENTION

A subject may be administered an immunogenic composition comprising allogeneic cancer cells, which secrete a modified heat shock protein (e.g., a heat shock protein lacking a native retention sequence for endoplasmic reticulum) at least partially encoded by a transfected expression vector or infected viral vector into the cells. As a nascent polypeptide chain, the modified heat shock protein may have its own or another protein's signal sequence to target the secretory pathway. And opposite an N-terminal signal sequence may be a peptide tag comprising one or more constant regions of human immunoglobulin heavy chain (e.g., IgG1 or IgG2). Optionally, the cancer cells express an allogeneic major histocompatibility complex (MHC) molecule (e.g., at least partially encoded by the same or different vector). They may or may not express CD80 (e.g., at least partially encoded by the same or different vector). More details of the expression of modified heat shock protein, HLA-A, and CD80 in various cancer cell lines are provided in WO 99/42121 and WO 2005/030136, which are incorporated by reference.

A subject may be administered in a range from $1 \times 10^7$ to $10 \times 10^7$ allogeneic cancer cells per dosage. A total number of cells from 1 to $10 \times 10^8$ may be administered to the subject. Allogeneic cancer cells may be administered at least twice daily, daily, every other day, twice weekly, weekly, every other week, or monthly between any two consecutive administrations. At least a total of nine, 18 or 27 dosages of allogeneic cancer cells may be administered. Dosages may be administered at intervals of less than two weeks, one week or less, at least twice weekly, at least every other day, at least daily, or at least twice daily. Treatment may continue for at least six weeks, ten weeks, 15 weeks, 18 weeks, 22 weeks, or 26 weeks (e.g., one to six months). During such periods of treatment, cells may be administered at intervals of less than two weeks, one week or less, at least twice weekly, at least every other day, at least daily, or at least twice daily. They may be injected by at least an intradermal, intravenous, intraperitoneal, or subcutaneous route. Each dosage may be split into aliquots for the separate injections that comprise a single administration. Treatment may be improved by frequent vaccination, B-cell depletion, or both.

Antigen (e.g., an epitope derived from neoantigen or tumor antigen of an allogeneic or syngeneic cancer cell) may induce a specific immune response in the subject. For example, the epitope bound in an immunogenic complex with the secreted heat shock protein may be obtained from allogeneic cancer cells coexpressing both secreted gp96 and antigen, or from syngeneic cancer cells of the subject expressing only antigen. The latter would presumably require that modified heat shock protein be taken up by a cancer cell different from where the gp96 was synthesized, and the complex formed in the cancer cell where the antigen was synthesized. Immunization may not require the subject to have functional $CD4^+$ T cells or lymph nodes. Therefore, after all modifications of gp96, including removal of the ER retention signal, the modified gp96 must still bind epitope in an immunogenic complex. Optional modifications include N-terminal additions or deletions, C- terminal additions, point mutations of 1 to 3 contiguous amino acids, or internal additions or deletions from 1 to 10 amino acids.

The subject may be a human subject. The cancer cells may be obtained from a human subject. The immunogen or vaccine may be administered to the same subject who donated the cancer cells or a different subject. Allogeneic cancer cells may have been obtained from a subject differing in transplantation antigen(s) as compared to the subject receiving the cells. Optionally, a major histocompatibility complex molecule (e.g., one or more MHC class I molecules such as HLA-A1, HLA-A2, HLA-A3, HLA-A27) may be expressed in the cancer cells by transfection of an expression vector or infection of a viral vector. The nucleic acid of the vector needs to encode at least partially the modified heat shock protein or allogeneic MHC molecule because the modification or histotype, respectively, may be introduced into an endogenous gene of the cancer cell by homologous recombination.

B cells may be depleted by techniques known in the art, such as ex vivo apheresis or administering antibody specific for a B-cell receptor (e.g., anti-CD19, anti-CD20, anti-CD22, anti-BLyS), dimerized ligand to crosslink a B-cell receptor (e.g., aptamer dimer), or immunosuppressive drug (e.g., cyclophosphamide or prednisolone) may be used. But in contrast to use of rituximab to treat lymphoma, or autoimmune disease, B-cell depletion in association with immunotherapy. in accordance with the present invention would spare other parts of the immune system to effect cell-based immunotherapy of cancer. For example, rituximab at a dosage from 100 mg/m$^2$ to 500 mg/m$^2$ (or from 200 mg/m$^2$ to 300 mg/m$^2$ or from 350 mg/m$^2$ to 400 mg/m$^2$) may be administered to a patient at a rate of 50 mg/hour to 400 mg/hour one or more times (e.g., once weekly for two weeks to two months). Rituximab may be supplemented with cyclophosphamide and prednisolone. B cells may be depleted then followed by immunotherapy (e.g., immunization or vaccination). The level of B cells may be monitored during immunotherapy and depletion repeated when above 1%, 5% or 10% of normal (i.e., non-depleted) levels.

Cancer cells of a subject undergoing abnormal proliferation may be a neoplasm or tumor (e.g., carcinoma, sarcoma, leukemia, lymphoma), especially lung cancer. Cancers include those originating from the gastrointestinal (e.g., esophagus, colon, intestine, ileum, rectum, anus, liver, pancreas, stomach), genitourinary (e.g., bladder, kidney, prostate), musculoskeletal, pulmonary (e.g., lung), or reproductive (e.g., cervix, ovary, testicle) organ systems. For example, lung cancer may non-small cell lung cancer (e.g., adenocarcinoma, squamous cell carcinoma, or large cell carcinoma), small cell lung cancer, and carcinoids. The cancer cell may be derived from the subject undergoing treatment or from another individual other than the subject. For the former case, allogenicity may be conferred by expressing an unrelated class I molecule of the major histocompatibility complex from a transfected expression vector or an infected viral vector. The cancer cells may be non-immunogenic or have low immunogenicity so long as they are engineered to secrete the modified heat shock protein. They may be from a carcinoma. An exemplary lung cancer cell is the AD100 adenocarcinoma, which is allogeneic for all subjects except the patient from which the cell line was derived and any rare individuals sharing that patient's MHC haplotype. Its derivation is described in WO 2005/030136. AD100 does not express HLA-A1, HLA-A2, or CD80. Pancreatic carcinoma may be treated with MIA PaCa-2 secreting gp96-Ig from ATCC CRL1420; ovarian carcinoma may be treated with OVCAR-3 secreting gp96-Ig from ICLC HTL97004.

Effectiveness of treatment may be evaluated by reduction in symptoms, delayed progression or regression of disease, or prolongation of survival. Or assay of $CD8^+$ T cell cytolysis of cancer cells or interferon gamma stimulated by them may be measured in vitro. Improvement in active immunotherapy may be used to treat cancer in combination with surgery, radiation therapy, and/or chemotherapy. Boosting may occur by administering the immunogenic complex at least monthly for one to two years.

Immunogenic compositions are comprised of allogeneic cancer cells and a pharmaceutically-acceptable carrier and/or vehicle. For example, the carrier may be alginate or PLGA beads or viral particles, and the vehicle may be water for injection or buffered saline solution. Prior to formulating the composition, the carrier or vehicle may be confirmed free of pathogen and pyrogen. Cells may be irradiated and suspended in buffered saline containing 0.5% human serum albumin. The composition is preferably suitable for systemic or local administration by injection or depot. It is preferred that the composition be tested for the absence of bacterial and viral contamination prior to administration. To avoid possible sources of contamination, it would be preferred to culture the allogeneic cancer cells in serum-free, defined medium. Cells may be stored in the same medium supplemented with 20% dimethyl sulfoxide as cryopreservative.

EXAMPLES

Anti-tumor vaccination is quite effective when administered to naïve, tumor-free mice resulting in protection from tumor growth upon subsequent challenge. Protection generally is long lasting and tumor specific indicating the participation of the adaptive immune response. This picture changes radically when vaccines are used for the therapeutic treatment of already established tumor. The same dose of vaccine that is able to effectively establish protective immunity generally is unable to provide therapeutic benefit. The reason for this lack of effectiveness of therapeutic vaccination is thought to stem from the induction of tumor induced suppressor cells, the generation of regulatory cells, the induction of T cell anergy or tolerance, or a combination thereof. Whatever the precise mechanisms of tumor induced immune suppression, the success of vaccine therapy for cancer therapy will depend on overcoming or neutralizing these tumor induced suppressive effects.

Based on pioneering work from the laboratories of Srivastava and Rammensee who showed that heat shock protein gp96-associated peptides are cross-presented to CD8$^+$ cells by dendritic cells, we have developed a vaccination system suitable for antitumor therapy. Transfecting a gp96-IgG1-Fc fusion protein into tumor cells results in secretion of gp96-Ig in complex with chaperoned tumor peptides. Parenteral administration of gp96-Ig secreting tumors triggers robust antigen-specific CD8$^+$ CTL expansion combined with activation of the innate immune system. Tumor secreted gp96 causes the recruitment of DC and NK cells to the site of gp96 secretion and mediates DC activation via binding to CD91 and TLR2 and TLR4. The endocytic uptake of gp96 and its chaperoned peptides triggers peptide cross presentation via MHC class I and strong, cognate CD8 activation independent of CD4$^+$ cells. In this model system CD8$^+$ CTL expansion can be precisely quantitated within 4 to 5 days of vaccination by use of adoptively transferred TCR transgenic, gfp-marked CD8$^+$ T cells. Using this test system we now show that in our model system tumor induced immune suppression is antigen non-specific and can be overcome by frequent immunization or by the absence of B cells.

Subjects, Cell Lines, and Antibodies

C57BL/6J (B6) mice were purchased from The Jackson Laboratory or Charles River Laboratories. Ig-p-chain deficient mice having a B6 background (DCBM) were purchased from The Jackson Laboratory.

Gfp (green fluorescent protein) mice were obtained from their producers. Transgenic C57BL/6J OT-I mice (obtained from Dr. M. Bevan) express a TCR (Vα2Vβ5.1.2) specific for H-2K$^b$-restricted chicken ovalbumin-derived peptide 257-264 (SIINFEKL). Gfp mice were crossed with OT-I mice to generate gfp-OT-I mice in the animal facility at the University of Miami in accordance with institutional guidelines.

The progeny mice were screened for the expression of the ova-TCR gene and by fluorescence for gfp. All mice were used at 6-12 week of age.

The EG7 cell line (obtained from M. Bevan) was transfected with the vector pCMG-His containing gp96-Ig. Control cells were transfected with vector alone. Lewis lung carcinoma (LLC) cells were obtained from the American Tissue Culture Collection and were transfected with ovalbumin in pAC-neo-ova or with both the ovalbumin vector and pCMG-His containing gp96-Ig. All cells were cultured in IMDM media (GIBCO) with 10% fetal calf serum (FCS) and gentamycin (GIBCO). To maintain transfected cells, antibiotics for selection (G418 or L-Histidinol, Sigma, St. Louis, Mo.) were added to the culture.

The following antibodies were used for staining: anti-CD16/32 (2.4G2), CyChrome-anti-CD3ε (145-2C11), -anti-CD5 (UCHT2), -anti-CD8a (53-6.7), PE-CD19 (4G7), PE or FITC-anti-NK1.1 (PK136), and PE or FITC-anti-CD11c (HL3) were purchased from BD PharMingen.

Purification and Adoptive Transfer of gfp-OT-I Cells and CD19$^+$ B Cells

Single-cell suspensions of splenocytes and lymph node (LN) cells were obtained from gfp-OT-I mice and pooled. They were depleted of red blood cells by ammonium chloride lysis. Gfp-OT-I cells were sorted by positive column selection using anti-CD8a magnetic microbeads and a MACS column (Miltenyi Biotec) according to the manufacturer's instructions. The purity of isolated OT-I cells was more than 95% as determined by flow cytometric analysis. Vα and Vβ5.1.2 expression on purified cells was quantified by flow cytometry. For purification of B cells, CD19$^+$ cells were purified with anti-CD19 microbeads (Miltenyi Biotec). To reconstitute B cells in BCDM mice, 10$^7$ purified cells were adoptively transferred through tail veins two days before transplantation of tumor cells.

Analysis of in vivo CD8$^+$ CTL Expansion

To measure CD8$^+$ CTL expansion, mice were adoptively transferred with 10$^6$ gfp-OT-I, immunized two days later by intraperitoneal (i.p.) injection of 1-4×10$^6$ non-irradiated EG7-gp96-Ig cells. Following immunization, cells were harvested from the peritoneal cavity, mesenteric, para-aortic lymph nodes (dLN), and peripheral blood at timed intervals. Red blood cells were removed from samples by ammonium chloride lysis. One million cells were incubated for 10 min at 4° C. with anti-CD16/32 mAb in PBS containing 0.5% BSA (PBA) to block FcR binding. Cells were then incubated with the indicated antibodies for 30 min. Samples were analyzed on a FACScan (Becton Dickinson) with CELL Quest software (BD Bioscience). The total number of the indicated immune cells per each tissue was calculated from the percentage of targeted cells and total number of cells in each tissue.

Tumor Inoculation and Treatment Protocol

Non-irradiated EG7, LLC or LLC-ova cells were injected subcutaneously (s.c.) in 200 μl PBS into the flanks of mice. Five days after inoculation of LLC-ova cells (day 5), 10$^6$ purified gfp-OT-I in a volume of 0.3 ml PBS were injected through tail veins. Two days later, mice were immunized by i.p. injection of 10$^6$ non-irradiated LLC-ova-gp96-Ig or EG7-gp96-Ig cells in a volume of 0.5 ml PBS according to the schedule indicated in the graphs. Control mice were treated with PBS, EG7 or LLC-ova. The size of tumors in the flank was measured in two dimensions twice per week for at least 20 days.

Statistical Analysis

Significance was evaluated by t-tests. A calculated value of $p<0.05$ was considered to indicate statistical significance.

Established Tumors Suppress Gp96-Mediated CD8-CTL Expansion Independent of TCR Specificity Transfection of heat shock fusion protein gp96-Ig into tumor cells results in secretion of gp96-Ig along with gp96-chaperoned peptides. Gp96-Ig is a modified protein generated by the replacement the endoplasmic reticulum retention signal (KDEL) of gp96 with the Fc portion of IgG1. Injection of mice with gp96-Ig secreting tumor cells results in the induction of tumor specific immunity and memory and protection from subsequent challenge with the same, but non-transfected tumor. Tumor immunity generated by secreted gp96-Ig is specific for gp96-chaperoned peptides including peptides derived from tumor endogenous antigens, such as EL4 specific antigens, and for surrogate antigens such as ovalbumin transfected into EL4 (EG7) or LLC (LLC-ova). The ovalbumin surrogate antigen offers a method to accurately determine $CD8^{30}$ CTL expansion in vivo via adoptive transfer of ovalbumin specific, OT-I TCR transgenic $CD8^+$ cells.

Established tumors are known to be suppressive for CTL expansion. To measure CTL responses in the presence and absence of established tumors, we used the TCR transgenic OT-I system in which transgenic $CD8^+$ CTL respond to ovalbumin-transfected syngeneic or allogeneic tumors secreting gp96-Ig-ova. As transplantable tumor models we used EG7, derived from the EL4 by ovalbumin transfection, which is classified as immunogenic and highly tumorigenic. In addition we also used the Lewis lung carcinoma (LLC and LLC-ova) which is considered less immunogenic and highly tumorigenic. The division rate of both cell lines is very rapid with a doubling time of 8-12 hours in culture.

After a single i.p. immunization with one million EG7-gp96-Ig-cells, secreting 60-80 ng gp96-Ig per $10^6$ cells in 24 hours, OT-I expand from low, preimmune levels in the $CD8^+$ gate (~0.2%) to high frequencies (15-40%) in tumor-free mice. Administration of irradiated EG7 not secreting gp96-Ig is not able to cause significant OT-I expansion. But subcutaneously established EG7 tumors present at a distant site in the flank significantly inhibits gp96-vaccine induced expansion of OT-I in the peritoneal cavity and systemically in spleen and lymph nodes. EG7 tumors secrete ovalbumin and express $K^b$-ova. It is possible therefore that adoptively transferred OT-I upon recirculation through the tumor bed or tumor draining lymph nodes become anergic due to receiving signals through their $K^b$-ova-specific TCR while not receiving costimulatory signal two. To evaluate this hypothesis, the syngeneic tumors EL4 and LLC, neither expressing ovalbumin, were established subcutaneously at distant sites. Subsequently, OT-I where adoptively transferred intravenously (i.v.) and mice immunized i.p. with EG7-gp96-Ig. Established EL4 and LLC were as effective in suppressing OT-I expansion by secreted gp96-ova as established EG7 indicating that suppression is not dependent on the appropriate TCR antigen, $K^b$-ova, in the tumor. While OT-I expansion in the peritoneal cavity and systemically was suppressed by the presence of LLC and EL4 at distant sites, total cell recruitment into the peritoneal cavity upon EG7-gp96-Ig immunization i.p. was actually increased when compared to tumor-free mice.

As also reported by others, the data indicate that established tumors can induce antigen non-specific suppression of CTL expansion. This induction of suppression correlates with increased cellular recruitment to the vaccine site in the peritoneal cavity. Transfer of vaccine induced peritoneal cells from tumor-bearing to tumor-free mice suppressed OT-I expansion in recipient mice indicating the presence of regulatory or suppressor cells. $CD8^+$ T cells thus are non-reactive due to a cellular suppressor response in tumor-bearing mice independent of antigen.

To overcome antigen non-specific immune suppression, we evaluated whether frequently repeated antigen-specific stimulation of $CD8^+$ CTL by vaccination could counteract the suppressive activity found in tumor-bearing mice.

Rejection of Established Tumors Requires Frequent gp96-Ig Immunizations

While many vaccination strategies, including secreted gp96-Ig, are able to establish protective immunity in mice against tumors and tumor antigens, it is more difficult to reject already established tumors by therapeutic vaccination. Given the observation of antigen non-specific suppression of CD8 expansion, we analyzed how different vaccination schedules affected tumor rejection and/or tumor growth.

We initially analyzed the effect of therapeutic vaccination by beginning vaccination on the same day as tumor transplantation. One million EG7 tumor cells were transplanted subcutaneously in the flank of syngeneic mice. On the same day (day 0), one million gp96-Ig secreting EG7 vaccine cells (EG7-gp96-1g), secreting gp96-Ig at a rate of 60-80 ng/$10^6$ cells×24 hr) were administered i.p. as vaccine and vaccination repeated on day 3, 7, 10 and 14. Compared to mice not receiving therapy, tumor growth is diminished by four EG7-gp96-Ig vaccinations starting on the same day as tumor transplantation. The therapeutic effect is gp96 and antigen. dependent. Irradiated EG7, not secreting gp96-Ig, or LLC-gp96-Ig, not expressing EG7-antigens but secreting gp96-Ig at the same rate as EG7-gp96-Ig, are unable to retard tumor growth when administered i.p. as vaccine at the identical dose and schedule as EG7-gp96-Ig. When vaccination with EG7-gp96-Ig is started two days or later after EG7 inoculation, the therapeutic effect using the same vaccination schedule is substantially diminished. These data demonstrate that even after two days established tumors are more difficult to control by vaccination than tumors that are freshly transplanted.

We next evaluated whether established tumors could be controlled by more frequent vaccination schedules. One million EG7 tumor cells were transplanted subcutaneously in the flank and allowed to become established for three to seven days, allowing at least seven or more tumor cell doublings. During this period vascularization of the tumor nodule occurs which is detectable visually. Mice were then vaccinated daily i.p. with one million EG7-gp96-Ig cells or, in specificity controls, with the same schedule and dose of LLC-gp96-Ig cells, or irradiated EG7 cells, or left unvaccinated. Daily vaccination with EG7-gp96-Ig effectively controlled growth of EG7 that had been established for three days, while daily vaccination with irradiated EG7 or with LLC-gp96-Ig had no effect on growth of established EG7. In further studies we allowed the transplanted EG7 tumors to become established for 5 and 7 days before starting vaccination with, EG7-gp96-Ig. Two vaccinations every day were required to retard tumor growth at this later stage of tumor establishment. The data show that frequent immunization can check tumor growth for a period of 24 days in mice. Further studies will be needed to determine whether continued long term vaccination schedules can completely eradicate tumors.

To validate data obtained with the immunogenic EG7 lymphoma, experiments were repeated with less immunogenic, established LLC. Repeated i.p. immunizations (day 3, 7, 10, 14) with LLC-gp96-Ig beginning on the third day after tumor transplantation resulted in retardation of tumor progression of LLC. Daily immunizations for LLC were not more effective in tumor retardation. The effect of immunization was tumor specific as EG7-gp96-Ig vaccination was unable to control LLC tumor growth. Tumor growth control also could not be achieved by irradiated LLC, but was dependent on gp96-Ig secretion.

These data suggest that frequent DC and NK activation combined with antigen cross presentation by secreted gp96-Ig and its chaperoned peptides, can overcome established tumor induced, antigen non-specific immune suppression.

Gp96-Mediated DC and NK Recruitment and CD8 CTL Expansion is Enhanced in B Cell Deficient Mice It has been reported by several groups that Th1 antitumor responses are enhanced in B cell deficient mice (BCDM) when compared to wild-type mice. We therefore studied the role of B cells in gp96-mediated CTL expansion and anti tumor immunity. The peritoneal cavity is populated by CD5-CD19+B cells and by CD5+CD19+B1-B cells, the latter producing IgM antibody and not undergoing isotype switching upon activation. Upon i.p. immunization with EG7-gp96-Ig the CD5-CD19+population increases about five fold by day 4 post immunization, while CD5+B1B cells increase only moderately. Gp96-mediated OT-I expansion is maximal on day 4 and 5 post immunization. It is preceded by recruitment and activation of DC and NK cells in the peritoneal cavity, the site of vaccination. In B-cell deficient mice, the recruitment of DC and especially NK cells was increased in three separate experiments and the recruited cells remained longer in the peritoneal cavity. The difference did not reach significance but was reproducible. Adoptive transfer of wild-type B cells to BCDM abolished increased recruitment of DC and NK cells. The finding suggests that B cells influence gp96-induced recruitment of innate immune cells and suggest that B cells may also be involved in regulating or suppressing $CDS^+$ CTL expansion.

We therefore evaluated whether expansion of gfp-marked OT-I was increased in BCDM. OT-I expansion after gp96-immunization in BCDM was about twice as strong as that seen in wild-type mice by day 4. Importantly, OT-I persisted at significantly higher frequencies on day 7 and 12 post immunization in the peritoneal cavity and in draining lymph nodes. Adoptive transfer of wild-type B cells to BCDM prior to immunization reduced OT-I expansion to levels at or below those seen in wild-type mice. The suppression of OT-I expansion by the presence of B cells is not mediated by IL-10 production since IL-10 deficient mice exhibit OT-I expansion similar to wild-type mice rather than enhanced expansion as seen in BCDM.

Gp96-Mediated Rejection of Established Tumors is Enhanced in the Absence of B Cells As shown above, growth control of established EG7 in wild-type mice minimally requires daily gp96-immunization. Similarly, LLC progression can be retarded by frequent immunizations. EG7 and EL4 cells are rejected in BCDM and do not establish tumors; however LLC and LLC-ova can be established in BCDM although they grow at a slower rate than in wild-type mice. LLC-ova was established subcutaneously in the flank for 7 days in BCDM and in wild-type mice. OT-I were adoptively transferred i.v. and two days later LLC-ova-gp96-Ig was administered as single dose i.p. and tumor growth monitored. In BCDM a single immunization resulted in complete rejection of established, seven day LLC-ova tumors in three mice and significant tumor shrinking in two. In the absence of treatment LLC-ova continued to grow progressively in BCDM albeit at a slower rate than in wild-type mice. B cell reconstitution of BCDM rendered the effect of vaccination similar to that seen in wild-type mice, namely retardation of progression.

Optimal tumor control of established LLC in BCDM by a single immunization is supported both by sufficiently high numbers of tumor specific CTL precursors (OT-I) and by antigen specific immunization (LLC-ova-gp96-Ig). In BCDM the presence of one million adoptively transferred OT-I without gp96-immunization does not result in tumor rejection in the majority of mice. Likewise gp96-immunization alone without OT-1 transfer is less effective than the combination.

Clinical Trial of Allogeneic Cancer Vaccine in Non-Small Cell Lung Cancer (NSCLC)

The allogeneic, lung cancer cell line AD100 is transfected with gp96-Ig and HLA-A1. At least 70% of the cells express greater than 60 ng gp96-Ig every 24 hours from one million cells. The recombinant cancer cells are irradiated and then injected intradermally into patients suffering from advanced, relapsed, or metastatic NSCLC (stage IIIB/IV). HLA matching is not required. If no concerns about toxicity arise, patients will be vaccinated with $5 \times 10^7$ allogeneic cancer cells once every week or every two weeks over 17 weeks. Alternatively, a total of $4.5 \times 10^8$ allogeneic cancer cells may be delivered by (a) nine injections over 18 weeks, (b) 18 injections over 18 weeks, or (c) 36 injections over 18 weeks.

Discussion

It is well appreciated that established tumors suppress antitumor immunity. Tumor specific T cells become anergic in the presence of established tumors. Anergy to the B cell lymphoma used in that study was antigen specific, MHC restricted and dependent on the presence of MHC matched bone marrow derived antigen presenting cells. In other studies antigen non-specific myeloid-suppressor cells and T regulatory cells have been implicated in suppression of anti tumor immunity. Our studies show that suppression of CTL responses in vivo can be achieved by established tumors through antigen-independent pathways. OT-I expansion in response to gp96-ova vaccination is inhibited by established tumors independent of the expression of ovalbumin by the tumors. This type of suppression may be achieved by T regulatory cells or by other suppressor cells such as myeloid-suppressor cells or M2 macrophages. In accord with this hypothesis, the suppressive activity is transferable to tumor-free mice by the transfer of peritoneal cells elicited in tumor-bearing mice by gp96-vaccination.

While the OT-I response to gp96-ova immunization is strongly inhibited in the presence of established tumors, it is not totally blocked, suggesting that there is balance, between immune suppression by the established tumor and CD8-CTL activation through antigen cross presentation by activated DC stimulated by secreted gp96-ova. We have shown previously that in tumor naïve mice gp96-ova results in the recruitment and activation of NK and DC followed by OT-I expansion. Established tumors, while actually enhancing recruitment of cells into the peritoneal cavity by LLC-gp96-Ig vaccination, inhibit OT-I expansion and suggest that in the presence of established tumors many of the recruited cells are likely to be suppressor cells. This hypothesis predicts that frequent immunizations with gp96-ova may overcome the suppressive activity by shifting the balance from suppression to increased immune activation through repeated gp96-mediated DC and NK stimulation, increased antigen cross presentation and CTL priming. Indeed frequent immunizations have significant effects on retardation of tumor progression. In the case of established EG7, daily or twice daily vaccinations were more effective in stopping tumor progression. For LLC, immunization every other or every third day were sufficient and daily immunization were not more effective. These tumor specific differences may be related to the rate by which suppressor cells are generated by the presence of the peripheral tumor. Alternatively, it may depend on the mechanism by which tumors mediate the induction of suppressor cells or the nature of the suppressor cells that have been induced. These questions are currently under study.

By studying the OT-I response to i.p. immunization with tumor secreted gp96-ova we noticed that large numbers of B cells are recruited into the peritoneal cavity. B cells have been reported to be inhibitory for anti tumor immunity prompting the question as to their role in gp96 mediated OT-I expansion. Using B cell deficient mice it became clear immediately that B cells inhibit both NK and DC recruitment and OT-I expansion following gp96-ova immunization. B cell reconstituted BCDM responded like wild-type mice to gp96-ova mediated OT-I expansion, ruling out the possibility that B cell deficiency had modified the responsiveness of BCDM to gp96-ova immunization in a manner unrelated to the absence of B cells. B cell deficiency resulted in enhanced OT-1 expansion and in strongly enhanced tumor rejection of seven day established LLC-ova tumors even after only a single gp96-Ig immunization. The data suggest that tumor mediated induction of suppressor cells is greatly diminished in the absence of B cells or that B cells them selves act as suppressor cells. Whether B cells participate in the induction of suppressor cells or whether B cells themselves are immunosuppressive for CTL responses needs further study; IL-10 however does not appear to be involved in B cell mediated suppression of tumor immunity. In ongoing studies we have found that OX40-L deficient B cells show reduced ability to suppress anti tumor immune responses. It remains to be determined how OX40-L expressed on B cells mediates suppression of anti tumor immunity and CTL expansion by gp96.

Our studies provide a model by which antigen-independent immune suppression can be studied and further defined. The role of B cells in particular in this process will be of great interest. In addition, our studies point to ways in which antitumor vaccines can be made more effective. Depletion of B cells with antibodies and subsequent frequent vaccination, for instance with tumor secreted gp96-vaccines, may result in more efficient control of tumor growth than that seen with conventional vaccination methods.

Patents, patent applications, books, and other publications cited herein are incorporated by reference in their entirety. In particular, the improvements described herein may be applied to administering the cancer cell vaccines of U.S. patent application Ser. No. 11/878,460, which is incorporated by reference.

In stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim reciting "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of reciting the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

We claim:

1. A method of immunizing a human subject having cancer, said method comprising the steps of:
   (i) administering to the subject doses of an immunogenic composition comprising allogeneic cancer cells that secrete a modified gp96 heat shock protein, wherein the modified gp96 heat shock protein comprises a modification which at least removes a domain of native gp96 that contains a retention signal for endoplasmic reticulum (ER), wherein the subject is administered a dose of the immunogenic composition at least once per week over a period of six months; and
   (ii) following step (i), administering to the subject a booster of the immunogenic composition at least monthly for one to two years.

2. The method of claim 1, wherein in step (i), the subject is administered a dose of the immunogenic composition at least 27 times.

3. The method of claim 1, wherein in step (i), the subject is administered a dose of the immunogenic composition at least twice per week.

4. The method of claim 1, wherein the modification replaces the removed domain with one or more heavy chain constant regions of IgG1 or IgG2.

5. A method of immunizing a human subject having cancer, the method comprising:
   (a) administering to the subject a B cell depletion treatment or procedure;
   (b) following (a), administering to the subject doses of an immunogenic composition comprising allogeneic cancer cells that secrete a modified gp96 heat shock protein, wherein the modified gp96 heat shock protein comprises a modification which at least removes a domain of native gp96 that contains a retention signal for ER, and wherein the subject is administered a dose of the immunogenic composition at least once per week over a period of six months; and
   (c) following (b), administering to the subject a booster of the immunogenic composition at least monthly for one to two years.

6. The method of claim 5, wherein step (b) comprises administering to the subject a dose of the immunogenic composition according to one of the following dosing regimens:
(i) at least twice per week;
(ii) at least nine doses administered at intervals of less than two weeks between each dose;
(iii) once per week dose administered over nine weeks;
(iv) at least 18 doses administered at intervals of less than two weeks between each dose;
(v) twice per week doses administered over 18 weeks;
(vi) one dose administered every two weeks over 17 weeks; and
(vii) 18 doses administered once per week over 18 weeks.

7. The method of claim 6, wherein the modification replaces the removed domain with one or more heavy chain constant regions of IgG1 or IgG2.

8. The method of claim 6, wherein the B cell depletion treatment or procedure comprises performing ex vivo apheresis.

9. The method of claim 5, wherein the B cell depletion treatment or procedure is repeated following administration of a first dose of the immunogenic composition.

10. The method of claim 5, wherein each of the doses of the immunogenic composition is administered by a route independently selected from the group consisting of intradermal, intravenous, intraperitoneal, and subcutaneous.

11. A method of immunizing a human subject having cancer, said method comprising the steps of:
(i) administering to the subject doses of an immunogenic composition comprising allogeneic cancer cells that secrete a modified gp96 heat shock protein, wherein the modified gp96 heat shock protein comprises a modification which at least removes a domain of native gp96 that contains a retention signal for endoplasmic reticulum (ER), wherein the subject is administered a dose of the immunogenic composition at least once per week over a period of 10 weeks; and
(ii) following step (i), administering to the subject a booster of the immunogenic composition at least monthly for one to two years.

12. The method of claim 11, wherein in step (i), the subject is administered a dose of the immunogenic composition at least 18 times.

13. The method of claim 11, wherein in step (i), the subject is administered a dose of the immunogenic composition at least 27 times.

14. The method of claim 11, wherein in step (i), the subject is administered a dose of the immunogenic composition at least twice per week.

15. The method of claim 11, wherein the modification replaces the removed domain with one or more heavy chain constant regions of IgG1 or IgG2.

16. A method of immunizing a human subject having cancer, said method comprising administering to the subject doses of an immunogenic composition comprising allogeneic cancer cells that secrete a modified gp96 heat shock protein, wherein the modified gp96 heat shock protein comprises a modification which at least removes a domain of native gp96 that contains a retention signal for ER, wherein the subject is administered a dose of the immunogenic composition at least once per week, at least 9 times, over a period of one to six months.

17. A method of immunizing a human subject having cancer, the method comprising:
(a) administering to the subject a B cell depletion treatment or procedure; and
(b) following (a), administering to the subject doses of an immunogenic composition comprising allogeneic cancer cells that secrete a modified gp96 heat shock protein, wherein the modified gp96 heat shock protein comprises a modification which at least removes a domain of native gp96 that contains a retention signal for ER, and wherein the subject is administered a dose of the immunogenic composition at least once per week, at least 9 times over a period of one to six months.

18. A method of immunizing a human subject having cancer, said method comprising administering to the subject doses of an immunogenic composition comprising allogeneic cancer cells that secrete a modified gp96 heat shock protein, wherein the modified gp96 heat shock protein comprises a modification which at least removes a domain of native gp96 that contains a retention signal for ER, wherein the subject is administered a dose of the immunogenic composition at least once per week over a period of at least 10 weeks.

* * * * *